(12) United States Patent
Yuan

(10) Patent No.: US 11,913,883 B2
(45) Date of Patent: Feb. 27, 2024

(54) HIGHLY SPECIFIC TISSUE IMAGING

(71) Applicant: BOARD OF REGENTS, THE UNIVERSITY OF TEXAS SYSTEM, Austin, TX (US)

(72) Inventor: Baohong Yuan, Arlington, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 842 days.

(21) Appl. No.: 16/977,959

(22) PCT Filed: Mar. 5, 2019

(86) PCT No.: PCT/US2019/020759
§ 371 (c)(1),
(2) Date: Sep. 3, 2020

(87) PCT Pub. No.: WO2019/173343
PCT Pub. Date: Sep. 12, 2019

(65) Prior Publication Data
US 2021/0333209 A1    Oct. 28, 2021

Related U.S. Application Data

(60) Provisional application No. 62/639,241, filed on Mar. 6, 2018.

(51) Int. Cl.
G01N 21/64    (2006.01)
A61K 49/00    (2006.01)
(Continued)

(52) U.S. Cl.
CPC ..... G01N 21/6428 (2013.01); A61K 49/0058 (2013.01); G01N 33/5091 (2013.01);
(Continued)

(58) Field of Classification Search
CPC .......... G01N 21/6428; G01N 33/5091; G01N 33/542; G01N 21/6486; G01N 2021/6441; G01N 2201/06113; A61K 49/0058
See application file for complete search history.

(56) References Cited

U.S. PATENT DOCUMENTS 10,267,786 B2 *  4/2019  Yuan ................... A61K 41/0028
10,379,109 B2 *  8/2019  Yuan ................... A61K 49/0034
(Continued)

FOREIGN PATENT DOCUMENTS

WO    2017210520 A1    12/2017

OTHER PUBLICATIONS

International Bureau, International Preliminary Report on Patentability for PCT/US2019/020759, dated Sep. 8, 2020.
(Continued)

*Primary Examiner* — David P Porta
*Assistant Examiner* — Fani Polyzos Boosalis
(74) *Attorney, Agent, or Firm* — Maynard Nexsen PC; John P. Zimmer

(57) ABSTRACT

A method of imaging comprises disposing a population of first targeting ultrasound-switchable fluorophores and a population of second non-targeting ultrasound-switchable fluorophores in an environment; detecting a first photoluminescence signal emitted by the population of first targeting fluorophores, and a second photoluminescence signal emitted by the population of second non-targeting fluorophores; determining a photoluminescence property of the population of second non-targeting fluorophores from the second photoluminescence signal; and using the determined photoluminescence property of the population of second non-targeting fluorophores to deconvolute the first photoluminescence signal into the population of first targeting fluorophores bound and unbound to a first target binding element in the environment.

29 Claims, 11 Drawing Sheets

(51) Int. Cl.
*G01N 33/50* (2006.01)
*G01N 33/542* (2006.01)

(52) U.S. Cl.
CPC ....... *G01N 33/542* (2013.01); *G01N 21/6486* (2013.01); *G01N 2021/6441* (2013.01); *G01N 2201/06113* (2013.01)

(56) References Cited

U.S. PATENT DOCUMENTS

| | | | |
|---|---|---|---|
| 2006/0184049 A1* | 8/2006 | Tsujita | A61B 5/0084 600/478 |
| 2013/0030289 A1* | 1/2013 | Zhu | A61B 5/0035 600/425 |
| 2014/0206031 A1 | 7/2014 | Yuan | |

OTHER PUBLICATIONS

International Bureau, Written Opinion of the International Searching Authority for PCT/US2019/020759, dated May 13, 2019.
Xu, et al., "In-vivo fluorescence imaging with a multivariate curve resolution spectral unmixing technique", Journal of Biomedical Optics, Nov. 1, 2009, vol. 14, No. 6, pp. 1-9, entire document.
Willmann, et al., "Dual-targeted Contrast Agent for Assessment of Tumor Angiogensis in vivo." Radiology, 01, Sep. 1, 2008, vol. 248, No. 3, pp. 936-944, entire document.
Tosi, et al., "Advances in Molecular Imaging of Locally Delivered Targeted Therapeutics for Central Nervous System Tumors,", International Journal of Molecular Sciences, Feb. 8, 2017, vol. 18, Iss. 2, pp. 1-19, entire document.
Yu et al., "New Generation ICG-Based Contrast Agents for Ultrasound-Switchable Fluorescence Imaging," Scientified Reports, Oct. 24, 2016, vol. 6, No. 35942, pp. 1-10, entire document.
International Search Report for PCT/US2019/020759, dated May 13, 2019.

* cited by examiner

US 11,913,883 B2

HIGHLY SPECIFIC TISSUE IMAGING

STATEMENT REGARDING FEDERALLY SPONSORED RESEARCH

This application is a U. S. National Phase of PCT/US2019/020759, filed Mar. 5, 2019 which claims priority pursuant to 35 U.S.C. § 119 to U.S. Provisional Patent Application No. 62/639,241, filed on Mar. 6, 2018, each of which are incorporated herein by reference in their entireties.

CROSS-REFERENCE TO RELATED APPLICATIONS

This application claims priority pursuant to 35 U.S.C. § 119 to U.S. Provisional Patent Application No. 62/639,241, filed on Mar. 6, 2018, which is hereby incorporated by reference in its entirety.

FIELD

The invention is generally related to systems and methods for high-resolution imaging and, more particularly, to imaging using ultrasound-switchable fluorescence (USF).

BACKGROUND

Biomedical imaging contrast agents are commonly used to either enhance or to enable one to visualize tissue bio-targets that are naturally invisible or too weak to be detected, such as proteins, molecules, some tissue structure, tissue function, among others. High specificity of the imaging contrast agent to a particular bio-target is desirable for precise imaging and diagnostics, but has proven to be challenging. This is because high specificity requires a high ratio of the signal from specifically bound to unbound contrast agents in the bio-target. Unfortunately, robust technology capable of differentiating bound from unbound contrast agents in vivo does not exist. Therefore, the desirable specificity of contrast agents to bio-targets is limited.

Conventional methods used in imaging technologies require passively waiting for the unbound contrast agents to be washed out of the bio-target. These conventional methods have limited specificity, because some unbound contrast agents may remain or stick somewhere for long periods of time or some non-specific binding may occur (i.e., false positive). Additionally, it is difficult to determine how long to wait. If a wait time is too short, the population of unbound agents in the bio-target will be significant, resulting in a false positive. If the wait time is too long, some bound agents may become detached or degraded, resulting in a false negative or low signal. Finally, the conventional method is time-consuming in longitudinal studies.

Therefore, a need exists for improved systems and methods for contrast agents.

SUMMARY

In one aspect, methods of imaging are described herein which, in some cases, can provide one or more advantages compared to other methods. For example, in some embodiments, a method described herein can provide imaging specificity to bio-targets present in deep biological tissue. The use of targeting ultrasound-switchable fluorophores and non-targeting ultrasound-switchable fluorophores (e.g., "contrast agents") permits ultrasound-switchable fluorescence (USF) imaging that can differentiate specifically bound contrasting agents (e.g., the targeting ultrasound-switchable fluorophores) from unbound contrast agents (e.g., the non-targeting ultrasound-switchable fluorophores). In addition, use of multiple, different targeting ultrasound-switchable fluorophores described herein can also permit differentiation of multiple bio-targets in biological tissue.

In some embodiments, such a method comprises: (a) disposing a population of first targeting ultrasound-switchable fluorophores and a population of second non-targeting ultrasound-switchable fluorophores in an environment; (b) exposing the environment to an ultrasound beam to create an activation region within the environment; (c) disposing the populations of first targeting fluorophores and the second non-targeting fluorophores within the activation region to switch the first targeting fluorophores and the second non-targeting fluorophores from an off state to an on state; (d) exposing the activation region with one or more beams of electromagnetic radiation, thereby exciting the population of first targeting fluorophores and second non-targeting fluorophores; (e) detecting a first photoluminescence signal emitted by the population of first targeting fluorophores, and a second photoluminescence signal emitted by the population of second non-targeting fluorophores; (f) determining a photoluminescence property of the population of second non-targeting fluorophores from the second photoluminescence signal; and (g) using the determined photoluminescence property of the population of second non-targeting fluorophores to deconvolute the first photoluminescence signal into the population of first targeting fluorophores bound and unbound to a first target binding element in the environment. In this manner, the first targeting ultrasound-switchable fluorophores have target specificity, and the percentages of bound and unbound first targeting fluorophores can be determined.

In some cases, a first targeting fluorophore reversibly binds to a first target binding element.

In some embodiments, a first targeting fluorophore comprises a first targeting moiety. An exemplary first targeting moiety can be a first antibody, such as anti-VEGFR2 or anti-$\alpha_v\beta_3$.

In some embodiments, a second non-targeting fluorophore comprises a non-targeting moiety. The second non-targeting moiety can in some cases be a negative control of the first targeting moiety. In one embodiment, the non-targeting moiety is an isotype-matched control antibody.

In some embodiments, a physicochemical behavior of unbound first targeting fluorophores in the environment is similar to a physicochemical behavior of unbound second non-targeting fluorophores in the environment.

Exemplary embodiments of environment include biological tissue, biological phantom material, or tissue-mimicking phantom material.

In some embodiments, a first targeting fluorophore has a first excitation wavelength maximum. A second non-targeting fluorophore can in some cases have a second excitation wavelength maximum that is different from the first excitation wavelength maximum to avoid or reduce spectral cross-talk. For example, in some embodiments, the first targeting fluorophore has a first excitation wavelength maximum, and the second non-targeting fluorophore has a second excitation wavelength maximum. In some instances, the first excitation wavelength maximum is equal to the second excitation wavelength maximum.

In some embodiments, a beam of electromagnetic radiation described herein has a wavelength maximum equal to the first excitation wavelength maximum and equal to the second excitation wavelength maximum. In some instances, the first excitation wavelength maximum is different from the second excitation wavelength maximum.

In some embodiments, an activation region described herein is exposed to a first beam of electromagnetic radiation with the first excitation wavelength maximum, and a second beam of electromagnetic radiation with the second excitation wavelength maximum. In one embodiment, the first beam of electromagnetic radiation and the second beam of electromagnetic radiation are exposed to the environment sequentially. In another embodiment, the first beam of electromagnetic radiation and the second beam of electromagnetic radiation are exposed to the environment simultaneously.

In some instances, an emission profile of a wavelength maximum of the emitted first photoluminescence signal is different from an emission profile of a wavelength maximum of the emitted second photoluminescence signal. In some cases, the emission profiles of the emitted first photoluminescence and the emitted second photoluminescence are individually selected from one of 680-710 nm, 740-770 nm, or >840 nm. In some embodiments, the first photoluminescence signal is detected with a first detector or first detector channel; and the second photoluminescence signal is detected with a second detector or second detector channel. The second detector can be off in some instances when the first photoluminescence signal is detected; and the first detector can be off in some cases when the second photoluminescence signal is detected. In other embodiments, the first detector detects the first photoluminescence signal simultaneously as the second detector detects the second photoluminescence signal.

In addition, in some embodiments, the method comprises using more than one targeting ultrasound-switchable fluorophore. For example, the method of imaging can further comprise ($a_2$) disposing a population of third targeting ultrasound-switchable fluorophores in the environment; ($c_2$) disposing the population of third targeting fluorophores within the activation region to switch the population of third targeting fluorophores from an off state to an on state; ($d_2$) exposing the activation region to the one or more beams of electromagnetic radiation, thereby exciting the population of third targeting fluorophores; ($e_2$) detecting a third photoluminescence signal emitted by the population of third targeting fluorophores; and ($f_2$) determining a photoluminescence property of the population of second non-targeting fluorophores from the second photoluminescence signal; and ($g_2$) using the determined photoluminescence property of the population of second non-targeting fluorophores to deconvolute the third photoluminescence signal into the population of third targeting fluorophores bound and unbound to a third target binding element in the environment.

In some embodiments, a third targeting fluorophore reversibly binds to a third binding element in the environment. The third binding element in some cases is different from the first binding element, and can optionally comprise a third targeting moiety. In some embodiments, the third targeting moiety is a third antibody different from the first antibody.

In some embodiments, the non-targeting moiety is a negative control of the third targeting moiety. In some instances, the non-targeting moiety is an isotype-matched control antibody of the third targeting moiety.

In some embodiments, a physicochemical behavior of unbound third targeting fluorophores in the environment is similar to a physicochemical behavior of unbound second non-targeting fluorophores in the environment.

In some cases, a third targeting fluorophore has a third excitation wavelength maximum, and a first targeting fluorophore described herein has a first excitation wavelength maximum and second non-targeting fluorophore described herein has a second excitation wavelength maximum. In some cases, the first excitation wavelength maximum, the second excitation wavelength maximum, and the third excitation wavelength maximum are each different wavelength maximums to avoid or reduce spectral cross-talk. In some instances, the first excitation wavelength maximum is equal to the second excitation wavelength maximum and the third excitation wavelength maximum. In other cases, the wavelength maximums for the first excitation wavelength maximum, the second excitation wavelength maximum, and the third excitation wavelength maximum are different.

In some embodiments, a beam of electromagnetic radiation has a wavelength maximum equal to the first excitation wavelength maximum, the second excitation wavelength maximum, and the third excitation wavelength maximum.

In some embodiments, an activation region described herein is exposed to a first beam of electromagnetic radiation with the first excitation wavelength maximum, a second beam of electromagnetic radiation with the second excitation wavelength maximum, and a third beam of electromagnetic radiation with the third excitation wavelength maximum. In some instances, the first beam of electromagnetic radiation, the second beam of electromagnetic radiation, and the third beam of electromagnetic radiation are exposed to the environment sequentially. In other instances, the first beam of electromagnetic radiation the second beam of electromagnetic radiation and the third beam of electromagnetic radiation are exposed to the environment simultaneously.

In some embodiments, each emission profile of a wavelength maximum of the emitted first photoluminescence signal, the emitted second photoluminescence signal, and the emitted third photoluminescence signal are different. In some instances, the emission profiles of the emitted first photoluminescence signal, the emitted second photoluminescence signal, and emitted third photoluminescence signal are individually selected from one of 680-710 nm, 740-770 nm, or >840 nm.

In some embodiments, a first photoluminescence signal is detected with a first detector or first detection channel; a second photoluminescence signal is detected with a second detector or second detection channel; and a third photoluminescence signal is detected with a third detector or third detection channel. In some instances, the second detector and third detector are off when the first photoluminescence signal is detected; the first detector and the third detector are off when the second photoluminescence signal is detected; and the first detector and the second detector are off when the third photoluminescence signal is detected. In other instances, the first detector, second detector, and third detector simultaneously detect the first photoluminescence signal, second photoluminescence signal, and third photoluminescence signal.

Methods of imaging described herein is not limited to two targeting ultrasound-switchable fluorophores. More generally, n different targeting ultrasound-switchable fluorophores may be used in a method described herein. Thus, in some embodiments, a method of imaging described herein comprises (a) disposing a population of n targeting ultrasound-switchable fluorophores and a population of non-targeting ultrasound-switchable fluorophores in an environment; (b) exposing the environment to an ultrasound beam to create an activation region within the environment; (c) disposing the populations of n targeting fluorophores and the non-targeting fluorophores within the activation region to switch the n targeting fluorophores and the non-targeting fluorophores from an off state to an on state; (d) exposing the activation region with up to n beams of electromagnetic radiation, thereby exciting the population of n targeting fluorophores and second non-targeting fluorophores; (e) detecting n photoluminescence signals respectively emitted by the populations of n targeting fluorophores, and a photoluminescence signal emitted by the population of non-targeting fluorophores; (f) determining a photoluminescence property of the population of non-targeting fluorophores from the corresponding photoluminescence signal; and (g) using the determined photoluminescence property of the population of non-targeting fluorophores to deconvolute the n photoluminescence signals into the population of n targeting fluorophores bound and unbound to corresponding n target binding elements in the environment. It is further to be understood that n can be any desired integer, such as 2, 3, 4, 5, 6, 7, 8, 9, or 10. Moreover, in some cases, the number n is selected based on a desired number of targeting elements detectable by the method and/or based on a desired number of detection channels.

These and other embodiments are described in more detail in the detailed description which follows.

BRIEF DESCRIPTION OF THE FIGURES

The invention will now be described by way of example, with reference to the following figures, of which.

DETAILED DESCRIPTION

Figure 1:
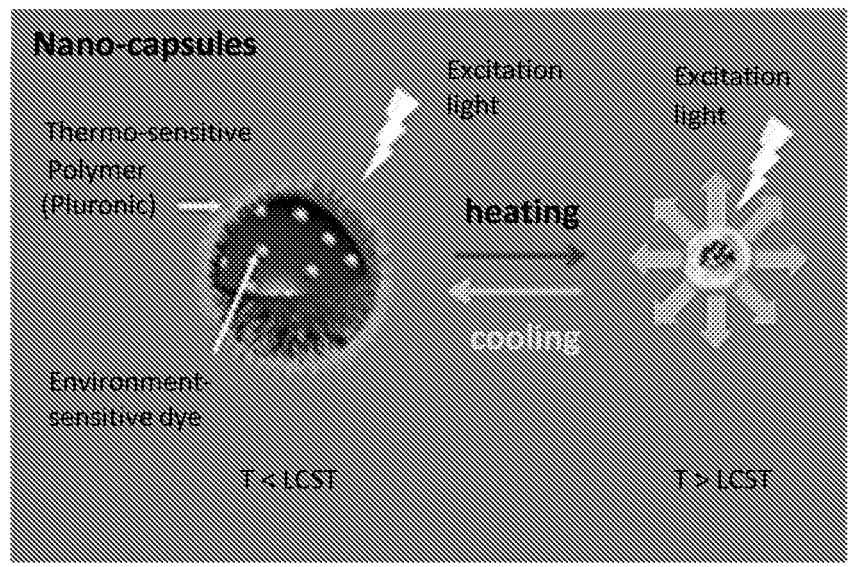
FIG. 1 illustrates schematically a thermal switching event of an ultrasound-switchable fluorophores.

Embodiments described herein can be understood more readily by reference to the following detailed description, examples, and figures. Elements, apparatus, and methods described herein, however, are not limited to the specific embodiments presented in the detailed description, examples, and figures. It should be recognized that these embodiments are merely illustrative of the principles of the current invention. Numerous modifications and adaptations will be readily apparent to those of skill in the art without departing from the spirit and scope of the invention.

In addition, all ranges disclosed herein are to be understood to encompass any and all subranges subsumed therein. For example, a stated range of "1.0 to 10.0" should be considered to include any and all subranges beginning with a minimum value of 1.0 or more and ending with a maximum value of 10.0 or less, e.g., 1.0 to 5.3, or 4.7 to 10.0, or 3.6 to 7.9.

All ranges disclosed herein are also to be considered to include the end points of the range, unless expressly stated otherwise. For example, a range of "between 5 and 10" or "from 5 to 10" or "5-10" should generally be considered to include the end points 5 and 10.

Further, when the phrase "up to" is used in connection with an amount or quantity, it is to be understood that the amount is at least a detectable amount or quantity. For example, a material present in an amount "up to" a specified amount can be present from a detectable amount and up to and including the specified amount.

The terms "first," "second," "third," and so on, are to be understood as generally distinguishing one object from another, rather than referring to a quantity of the object. For example, when describing three separate objects, each object can be distinguished from the other objects by the names "first object," "second object," and "third object". In cases where a quantity of an object is being described, the description with particularly identify that a quantity of the object is being discussed.

In one aspect, methods of imaging are described herein. In some embodiments, such a method comprises: (a) disposing a population of first targeting ultrasound-switchable fluorophores and a population of second non-targeting ultrasound-switchable fluorophores in an environment; (b) exposing the environment to an ultrasound beam to create an activation region within the environment; (c) disposing the populations of first targeting fluorophores and the second non-targeting fluorophores within the activation region to switch the first targeting fluorophores and the second non-targeting fluorophores from an off state to an on state; (d) exposing the activation region with one or more beams of electromagnetic radiation, thereby exciting the population of first targeting fluorophores and second non-targeting fluorophores; (e) detecting a first photoluminescence signal emitted by the population of first targeting fluorophores, and a second photoluminescence signal emitted by the population of second non-targeting fluorophores; (f) determining a photoluminescence property of the population of second non-targeting fluorophores from the second photoluminescence signal; and (g) using the determined photoluminescence property of the population of second non-targeting fluorophores to deconvolute the first photoluminescence signal into the population of first targeting fluorophores bound and unbound to a first target binding element in the environment. In this manner, the first targeting ultrasound-switchable fluorophores have target specificity, and the percentages of bound and unbound first targeting fluorophores can be determined.

It is also possible to use more than one targeting ultrasound-switchable fluorophore. For example, in some embodiment, the methods of imaging can further comprise $(a_2)$ disposing a population of third targeting ultrasound-switchable fluorophores in the environment; $(c_2)$ disposing the population of third targeting fluorophores within the activation region to switch the population of third targeting fluorophores from an off state to an on state; $(d_2)$ exposing the activation region to the one or more beams of electromagnetic radiation, thereby exciting the population of third targeting fluorophores; (e$_2$) detecting a third photoluminescence signal emitted by the population of third targeting fluorophores; and (f$_2$) determining a photoluminescence property of the population of second non-targeting fluorophores from the second photoluminescence signal; and (g$_2$) using the determined photoluminescence property of the population of second non-targeting fluorophores to deconvolute the third photoluminescence signal into the population of third targeting fluorophores bound and unbound to a third target binding element in the environment.

A method described herein is not necessarily limited to two targeting ultrasound-switchable fluorophores. More generally, n different targeting ultrasound-switchable fluorophores may be used in a method described herein. Thus, in some embodiments, a method of imaging described herein comprises (a) disposing a population of n targeting ultrasound-switchable fluorophores and a population of non-targeting ultrasound-switchable fluorophores in an environment; (b) exposing the environment to an ultrasound beam to create an activation region within the environment; (c) disposing the populations of n targeting fluorophores and the non-targeting fluorophores within the activation region to switch the n targeting fluorophores and the non-targeting fluorophores from an off state to an on state; (d) exposing the activation region with up to n beams of electromagnetic radiation, thereby exciting the population of n targeting fluorophores and second non-targeting fluorophores; (e) detecting n photoluminescence signals respectively emitted by the populations of n targeting fluorophores, and a photoluminescence signal emitted by the population of non-targeting fluorophores; (f) determining a photoluminescence property of the population of non-targeting fluorophores from the corresponding photoluminescence signal; and (g) using the determined photoluminescence property of the population of non-targeting fluorophores to deconvolute the n photoluminescence signals into the population of n targeting fluorophores bound and unbound to corresponding n target binding elements in the environment. It is further to be understood that n can be any desired integer, such as 2, 3, 4, 5, 6, 7, 8, 9, or 10. Moreover, in some cases, the number n is selected based on a desired number of targeting elements in the detectable by the method and/or based on a desired number of detection channels.

It is further to be understood that, as a general matter, the foregoing steps (b)-(f) or (d)-(f) may be repeated any desired number of times to image the ultrasound-switchable fluorophores according to a method described herein. In such instances, the detected signals can be combined (or binned or integrated) and then further processed, or processed as a function of time to determine ratios of bound and unbound targeting ultrasound-switchable fluorophores, as described further hereinbelow. The repeated steps can also be performed after moving the activation region to a different location within the environment, such as may be achieved by raster scanning the environment or a portion thereof with the ultrasound beam.

In some embodiments, the photoluminescent emission signals of individual ultrasound-switchable fluorophores described herein are individually resolved or isolated. Such individual resolution or isolation can be achieved by selectively exciting a given ultrasound-switchable fluorophore and/or by selectively detecting the resulting emission of the given ultrasound-switchable fluorophore. For example, in some cases, the beam of electromagnetic radiation has a wavelength maximum sufficient to excite the first targeting fluorophore and the second non-targeting fluorophore in the on state. Moreover, in other cases, exposing the environment to a beam of electromagnetic radiation comprises exposing the environment to first and second beams of electromagnetic radiation (which can be referred to as a first excitation beam and a second excitation beam, respectively), wherein the first excitation beam and the second excitation beam have different wavelength maximums. This can be particularly desirable when the first and second ultrasound-switchable fluorophores have differing absorption or excitation profiles. For example, in some embodiments, the first excitation beam can primarily excite the first targeting ultrasound-switchable fluorophore, and the second excitation beam can primarily excite the second non-targeting ultrasound-switchable fluorophore at a different wavelength maximum. Further, in some cases, the first and second excitation beams are provided to the environment sequentially or non-simultaneously. However, in other cases, the first and second excitation beams are provided to the environment simultaneously.

In some such embodiments, the first photoluminescence signal is primarily associated with or correlated to photoluminescence of the first targeting ultrasound-switchable fluorophore, and the second photoluminescence signal is primarily associated with or correlated to photoluminescence of the second non-targeting ultrasound-switchable fluorophore. Further, in some such embodiments, the first and second photoluminescence signals are detected using differing detectors or detection channels, and the detectors or detection channels are turned on or off in accordance with the sequence of the excitation beams, such that a given detector or detection channel is operable to receive and process a photoluminescence signal (i.e., is "on") or not (i.e., is "off") only or primarily only from a desired fluorophore, namely, the fluorophore primarily excited by the desired excitation beam. For instance, in some cases, the first photoluminescence signal is detected with a first detector or detection channel, and the second photoluminescence signal is detected with a second detector or detection channel. Moreover, the first detector or detection channel is off when the second photoluminescence signal is detected, and the second detector or detection channel is off when the first photoluminescence signal is detected. In other embodiments, the first detector or detection channel and the second detector or detection channel are on at the same time, and simultaneously detect their respective photoluminescence signals.

It is to be understood that the foregoing principle can be extended to n ultrasound-switchable fluorophores, n photoluminescence signals, and n detectors or detection channels. For instance, in some embodiments, exposing the environment to a beam of electromagnetic radiation comprises exposing the environment to n excitation beams, wherein the n excitation beams have differing wavelength maximums, wherein the nth excitation beam primarily excites the nth ultrasound-switchable fluorophore, and wherein the n excitation beams are provided to the environment sequentially or non-simultaneously. Moreover, in some such cases, n photoluminescent signals are detected with n differing detectors or detection channels, and each nth photoluminescence signal is primarily associated with or correlated to photoluminescence of the nth ultrasound-switchable fluorophore. Further, the n detectors or detection channels are turned on or off in accordance with the sequence of the excitation beams, such that each nth detector or detection channel is on when the nth photoluminescence signal is to be detected (or when the nth fluorophore is primarily excited) and off when the nth photoluminescence signal is not to be detected (or when the nth fluorophore is not primarily excited). As described above, n can be any desired integer, such as 2, 3, 4, 5, 6, 7, 8, 9, or 10.

Moreover, it is further to be understood that it is also possible for n ultrasound-switchable fluorophores to be used, but for less than n detectors or detection channels (and/or less than n excitation beams or excitation sources) to be used (provided n is at least 2). In such instances, the detectors or detection channels (and/or excitation beams or excitation sources) can be shared and/or used in an alternating or other temporally resolved manner.

Resolution or isolation of individual photoluminescence signals primarily associated with individual ultrasound-switchable fluorophores can be further achieved or improved, if needed, by using excitation and/or emission filters for one or more excitation beams and/or one or more detectors or detection channels, as described further hereinbelow. It is also possible to deconvolute or resolve individual photoluminescence signals primarily associated with individual ultrasound-switchable fluorophores by carrying out one or more signal processing steps, as described further hereinbelow and/or as known to one of ordinary skill in the art. For example, in some cases, multivariate curve resolution is used, as described in Xu et al., "In-vivo fluorescence imaging with a multivariate curve resolution spectral unmixing technique," *J. Biomed. Opt.* 14 (2009).

Turning now to specific steps of methods, methods described herein comprise disposing a population of ultrasound-switchable fluorophores in an environment. Any environment not inconsistent with the objectives of the current disclosure may be used. In some embodiments, the environment is a biological environment. An environment of a method described herein may also be a non-biological environment. In some cases, for example, a biological environment is an in vivo environment, such as a tissue, organ, blood vessel, or other portion of a living organism. In some embodiments, the biological environment comprises a tumor or tumor vasculature. In other cases, a biological environment comprises an in vitro environment, such as a tissue culture. The biological environment of a method described herein can also comprise or be replaced by a biological phantom material or tissue-mimicking phantom material, such as an agar, silicone, polyvinyl alcohol (PVA) gel, polyacrylamide (PAA) gel, or a dispersion of an oil in gelatin. Other phantom materials may also be used.

Moreover, in some embodiments, a biological environment comprises deep tissue. "Deep" tissue, for reference purposes herein, comprises tissue (or, in the case of a phantom material, an interior region of the phantom material) that is located at least about 1 cm below the exterior or outer surface of the organism, tissue culture, or other larger structure associated with the biological environment (such as, in the case of a phantom material, the outer surface of the phantom material). In some embodiments, for instance, deep tissue is located between about 1 cm and about 10 cm or between about 1 cm and about 5 cm below an outer surface. In some cases, deep tissue is located more than 10 cm below an outer surface. Further, an outer surface, in some embodiments, comprises the surface of the skin of an organism.

In addition, any ultrasound-switchable fluorophore or combination of differing ultrasound-switchable fluorophores not inconsistent with the objectives of the current disclosure may be used. An "ultrasound-switchable" fluorophore, for reference purposes herein, comprises a fluorophore operable to switch between an on state and an off state in response to exposure to an ultrasound beam. The ultrasound beam can be either directly or indirectly responsible for the switching response of the fluorophore. For example, in some cases, the ultrasound beam interacts directly with the fluorophore, resulting in a switch between fluorescence states of the fluorophore. In other cases, the ultrasound beam interacts directly with the immediate environment or microenvironment of the fluorophore and changes at least one property of the fluorophore's microenvironment. In such cases, the fluorophore can switch between on and off fluorescence states in response to the environmental change induced by the ultrasound beam. A non-limiting example of an environmental change would be a change in temperature. Thus, the fluorophore can be indirectly switchable in response to exposure to an ultrasound beam.

The "on" state of a fluorophore, for reference purposes herein, comprises either (1) a state at which the fluorescence intensity of the fluorophore is relatively high compared to the "off" state of the fluorophore, at which the fluorescence intensity is relatively low (assuming the fluorophore is similarly excited in both the on state and the off state); or (2) a state at which the fluorescence lifetime of the fluorophore is relatively long compared to the "off" state of the fluorophore, at which the fluorescence lifetime is relatively short (again assuming the fluorophore is similarly excited). Further, in both cases, the on and off states substantially define a step function in the fluorescence intensity or lifetime profile when plotted as a function of a critical switching parameter such as temperature. A fluorophore having a longer lifetime in an on state than an off state can be particularly suitable for use in methods described herein using time-gated or time-delayed detection of emitted photons from fluorophores, such as time-gated detection in which only those photons received after a relatively long delay following excitation are counted by the detector as part of the USF signal. In some cases, the on state of a fluorophore exhibits at least about 70 percent, at least about 80 percent, or at least about 90 percent of the theoretical maximum fluorescence intensity of the fluorophore, and the off state of the fluorophore exhibits no more than about 50 percent, no more than about 30 percent, no more than about 10 percent, or no more than about 5 percent of the theoretical maximum fluorescence intensity of the fluorophore.

The physical cause for the existence of an on state versus an off state can vary. For example, in some cases, the fluorescence intensity or fluorescence lifetime of a fluorophore changes due to a conformational or chemical change of the fluorophore in response to a change in environmental conditions, such as exhibited by some thermoresponsive polymers, pH-sensitive chemical species, or pressure sensitive materials. In some cases, the fluorescence intensity or fluorescence lifetime of a fluorophore changes in response to internal fluorescence quenching, wherein such quenching can be directly or indirectly induced by the presence of ultrasound.

For example, in some embodiments, a fluorophore described herein comprises a Förster resonance energy transfer (FRET) donor species and a FRET acceptor species, and the distance between the FRET donor species and the FRET acceptor species is altered by the presence of an ultrasound beam. The FRET donor species can be a first fluorescent species or other chromophore, and the FRET acceptor species can be a second fluorescent species or other chromophore. In such cases, as understood by one of ordinary skill in the art, FRET energy transfer between the donor species and the acceptor species can result in quenching of the fluorescence of the donor species. Thus, the acceptor species can be considered to be a fluorescence quenching species of the fluorophore. Any donor-acceptor pair not inconsistent with the objectives of the current disclosure may be used in FRET-based fluorophores described herein. For example, in some cases, the donor species comprises Alexa Fluor 546 and the acceptor species comprise Alexa Fluor 647. Other combinations of acceptor species and donor species are also possible.

In some embodiments, a fluorophore described herein comprises a microbubble comprising one or more FRET donor species and one or more FRET acceptor species attached to the exterior surface of the microbubble, wherein the microbubble is operable to change in size in response to the presence of an ultrasound beam. The change in size can increase or decrease the distance between the FRET donor species and the FRET acceptor species, thus reducing or increasing the FRET energy transfer efficiency. As a result, the fluorescence quenching and the overall fluorescence intensity of the microbubble can vary based on the size of the microbubble.

A microbubble described herein can have any size and be formed of any chemical species not inconsistent with the objectives of the current invention. In some cases, a microbubble has a diameter between about 1 μm and about 10 μm or between about 1 μm and about 5 μm. Other sizes of microbubbles may also be used. Moreover, in some embodiments, a microbubble described herein comprises a gas core surrounded by a shell formed from a polymeric material, such an organic polymeric material. In other cases, the shell is formed from a lipid material. In some embodiments, a microbubble comprises a shell formed from one or more of albumin, galactose, lipid, and sulfur hexafluoride. In addition, the gas core of a microbubble described herein can comprise one or more of air, nitrogen, and a perfluorocarbon such as octafluoropropane. Moreover, in some cases, a microbubble described herein is formed from a commercially available microbubble, such as a SonoVue™, Optison™, Imagent™, Definity™, or Targestar™ microbubble. A FRET donor and/or acceptor species described herein can be attached to the surface of such a microbubble in any manner not inconsistent with the objectives of the current invention. In some cases, for instance, a donor and/or acceptor species is attached to the exterior surface of a commercially available microbubble using one or more of a carbodiimide, maleimide, or biotin-streptavidin coupling scheme. Moreover, any other coupling scheme not inconsistent with the objectives of the current disclosure can be used to attach a donor and/or acceptor species to a microbubble.

In an embodiment, gas-filled micro-particles, such as the above described microbubbles, generate a short but high temperature pulse in and around the particle surface when the microbubble is irradiated with an ultrasound pulse at diagnostic intensity level. This short temperature pulse spatially decays very fast (only ~0.2° C. left at a distance of 1 micron away from the bubble surface). In ultrasound imaging, tissue overheating caused by microbubbles is minimalized from this fast temperature decay. However, this microscopic heating principle is effective for heating ultrasound switchable fluorophores, because ultrasound switchable fluorophores are small nanoparticles that can be attached on the microbubble's surface. As seen for example in FIG. 8, ultrasound switchable fluorophores (e.g. USF Contrast Agents) can be attached to a microbubble via a biotin/streptavidin linkage. Moreover, any other linkage not inconsistent with the objectives of the current disclosure can be used to attach ultrasound switchable fluorophores to a microbubble.

In other embodiments, a highly ultrasound-absorbing polymer, biodegradable polyurethane with pendent carboxyl groups (PU—COOH), can alternatively be used instead of the microbubbles. These ultrasound-absorbing polyurethanes make relatively rigid gas-filled sub-micro-particles (~700 nm in diameter). These ultrasound-absorbing polyurethanes are generally smaller in diameter than microbubbles, reducing their acoustic attenuation compared to microbubbles. However, their relatively rigid structures can sometimes display more resilient bio-stability than microbubbles. Similar to the microbubbles, biotin can be incorporated onto the surface of the ultrasound-absorbing polyurethanes, and the USF contrast agents can be attached using the streptavidin linkage. Moreover, any other coupling scheme not inconsistent with the objectives of the current disclosure can be used to attach a donor and/or acceptor species to a microbubble.

In some embodiments, a fluorophore described herein comprises a thermoresponsive polymer. A "thermoresponsive" polymer, for reference purposes herein, comprises a polymer having a physical or chemical property that changes in a temperature-dependent manner, wherein the change is a discontinuous or binary change. For example, in some cases, the physical conformation or polarity of a thermoresponsive polymer changes in a temperature-dependent manner, and the thermoresponsive polymer exhibits a first conformation below a threshold temperature and a second, substantially different conformation above the threshold temperature. In some embodiments, for instance, a thermoresponsive polymer exhibits an expanded coil or chain confirmation below a threshold temperature and exhibits a compact or globular conformation above the threshold temperature. In some such cases, the threshold temperature can be referred to as the "lower critical solution temperature" (LCST) of the polymer.

Any thermoresponsive polymer not inconsistent with the objectives of the current invention may be used. In some embodiments, a thermoresponsive polymer comprises a poly(N-isopropylacrylamide) or a copolymer of N-isopropylacrylamide with one or more of acrylamide, N-tert-butylacrylamide, acrylic acid, and allylamine. In other cases, a thermoresponsive polymer comprises a poly(N-vinylcaprolacatam) (PVCL) or a poloxamer such as a Pluronic polymer. Other thermoresponsive polymers may also be used.

Additionally, in some cases, a thermoresponsive polymer of a fluorophore described herein comprises one or more fluorescent moieties or is conjugated to one or more fluorescent species, such as one or more fluorescent dye molecules. The thermoresponsive polymer can be conjugated to the fluorescent species in any manner not inconsistent with the objectives of the current invention. For example, in some cases, a thermoresponsive polymer is coupled to a fluorescent species through one or more covalent bonds such as one or more ester bonds or one or more amide bonds.

Some non-limiting examples of an ultrasound-switched fluorescence process using a thermoresponsive fluorophore are illustrated in U.S. Patent Application Publication No. 2015/0309014 to Yuan et al. (hereinafter "the '014 publication"). As described in the '014 publication, a thermoresponsive polymer can be conjugated to a fluorescent species to provide a fluorophore. The fluorophore has a chain conformation and a globular conformation described hereinabove, and the conformation is temperature-dependent. Further, the transition from one conformation to the other results in a change in the fluorescence intensity or lifetime of the fluorescent species. As described further herein, the change in fluorescence intensity or lifetime can be due to differences in the microenvironment of the fluorescent species when the polymer is in the chain conformation compared to the globular conformation. For example, in some cases, the polarity and/or viscosity of the polymer environment experienced by the fluorophore changes depending on whether the polymer is in the chain conformation or the globular conformation.

Further, in some embodiments, a fluorophore described herein comprises a fluorescent material dispersed in and/or attached to the surface of a thermoresponsive polymer nanoparticle. Moreover, the fluorescence properties of the fluorescent material can be dependent on a change of the conformation, polarity, or other physical or chemical property of the polymer nanoparticle. In addition, the property change can be a temperature-dependent change. In this manner, a change in temperature of the thermoresponsive polymer nanoparticle can result in a change in fluorescence intensity and/or lifetime of the fluorescent material, including a change between an on state of the fluorescent material and an off state of the fluorescent material.

For example, in some embodiments, a thermoresponsive polymer nanoparticle can exhibit a temperature-dependent polarity, and the fluorescent material dispersed in the nanoparticle can exhibit a polarity-dependent fluorescence intensity and/or lifetime. Thus, a change in the temperature of the nanoparticle can result in a change in the fluorescence intensity and/or lifetime of the fluorophore.

In another exemplary embodiment, a thermoresponsive polymer nanoparticle can have a hydrophilic interior below a threshold temperature and a hydrophobic interior above the threshold temperature. Thus, such a nanoparticle can exhibit a temperature-dependent size when dispersed in a polar or non-polar solvent. For example, when dispersed in water or another polar solvent below the threshold temperature, the nanoparticle can exhibit a larger size due to the presence of water in the hydrophilic interior of the nanoparticle. Similarly, above the threshold temperature, the nanoparticle can exhibit a smaller size due to the exclusion of water from the now hydrophobic interior of the nanoparticle. In this manner, a fluorescent material dispersed in the nanoparticle can have a temperature-dependent concentration, which can result in temperature-dependent fluorescence properties of the overall fluorophore. This process is illustrated schematically in the '014 publication, specifically in FIG. 2.

In yet another exemplary embodiment, an ultrasound-switchable fluorophore is formed by incorporating a fluorescent material such as a fluorescent dye within the interior of a polymeric nanoparticle or micelle, such that the polymeric nanoparticle or micelle acts as a nanocapsule for the fluorescent material. Moreover, the polymeric nanoparticle can be formed from a thermoresponsive polymer, such as a thermoresponsive polymer described hereinabove. Non-limiting examples of polymers suitable for forming nanocapsules described herein include Pluronic F127, Pluronic F98, poly(N-isopropylacrylamide) (PNIPAM), and copolymers of PNIPAM with acrylamide (AAm) or N-tert-butylacrylamide (TBAm). Moreover, in some instances, a nanoparticle or nanocapsule can be formed by copolymerizing a thermoresponsive polymer described hereinabove with a polyethylene glycol (PEG) and/or by conjugating a PEG as a pendant group to a thermoresponsive polymer. Such a fluorophore, in some cases, can have a switching threshold that is controlled at least in part by the inclusion of PEG, as described further in the '014 publication.

A polymer nanoparticle such as a thermoresponsive polymer nanoparticle or a polymer nanocapsule described herein can have any size or shape not inconsistent with the objectives of the current disclosure. In some embodiments, for instance, a thermoresponsive polymer nanoparticle is substantially spherical and has a diameter between about 10 nm and about 300 nm, between about 50 nm and about 250 nm, between about 50 nm and about 200 nm, or between about 70 nm and about 150 nm. In some cases, a polymer nanocapsule is substantially spherical and has a diameter of less than about 100 nm or less than about 50 nm. In some instances, a polymer nanocapsule has a size between about 20 nm and about 90 nm, between about 20 nm and about 80 nm, or between about 20 nm and about 70 nm. Other sizes and shapes are also possible.

Further, any fluorescent material not inconsistent with the objectives of the current invention may be dispersed in and/or attached to a thermoresponsive polymer nanoparticle or other polymer nanoparticle to form a fluorophore described herein. In some embodiments, as described herein, the fluorescent material exhibits a polarity-sensitive fluorescence intensity and/or lifetime. In other cases, the fluorescent material exhibits a temperature-dependent, viscosity-dependent, pH-dependent, and/or an ionic strength-dependent fluorescence intensity and/or lifetime.

Non-limiting examples of fluorescent materials suitable for use in some embodiments described herein include organic dyes such as N,N-dimethyl-4-benzofurazansulfonamide (DBD); 4-(N,N-dimethylaminosulfonyl)-7-(2-aminoethylamino)-2,1,3-benzoxadiazole (DBD-ED); indocyanine green (ICG); a Dylight-700 such as Dylite-700-2B; IR-820; 3,3'-Diethylthiatricarbocyanine iodide (DTTCI); LS-277; LS-288; a cypate; a rhodamine dye such as rhodamine 6G or rhodamine B; or a coumarin. In some instances, a fluorescent material comprises an azadipyrromethene. In addition, in some cases, a fluorescent material comprises an inorganic species such as a semiconductor nanocrystal or quantum dot, including a II-VI semiconductor nanocrystal such as ZnS or CdSe or a III-V semiconductor nanocrystal such as InP or InAs. In other instances, a fluorescent material comprises a Lanthanide species. Additional non-limiting examples of fluorescent materials suitable for use in an ultrasound-switchable fluorophore described herein include the fluorescent materials described in Amin et al., "Syntheses, Electrochemistry, and Photodynamics of Ferrocene-Azadipyrromethane Donor-Acceptor Dyads and Triads," *J. Phys. Chem. A* 2011, 115, 9810-9819; Bandi et al., "A Broad-Band Capturing and Emitting Molecular Triad: Synthesis and Photochemistry," *Chem. Commun.*, 2013, 49, 2867-2869; Jokic et al., "Highly Photostable Near-Infrared Fluorescent pH Indicators and Sensors Based on $BF_2$-Chelated Tetraarylazadipyrromethane Dyes," *Anal. Chem.* 2012, 84, 6723-6730; Jiang et al., "A Selective Fluorescent Turn-On NIR Probe for Cysteine," *Org. Biomol. Chem.*, 2012, 10, 1966-1968; and Kucukoz et al., "Synthesis, Optical Properties and Ultrafast Dynamics of Aza-boron-dipyrromethane Compounds Containing Methoxy and Hydroxy Groups and Two-Photon Absorption Cross-Section," *Journal of Photochemistry and Photobiology A: Chemistry* 247 (2012), 24-29; the entireties of which are hereby incorporated by reference. Other fluorescent materials may also be used.

An ultrasound-switchable fluorophore described herein can have any fluorescence emission profile not inconsistent with the objectives of the current invention. For example, in some embodiments, a fluorophore exhibits an emission profile including visible light or centered in the visible region of the electromagnetic spectrum, such as between 450 nm and 750 nm. In some cases, a fluorophore exhibits an emission profile including infrared (IR) light or centered in the IR region of the electromagnetic spectrum. For example, in some instances, a fluorophore described herein exhibits an emission profile centered in the near-IR (NIR, 750 nm-1.4 µm), short-wavelength IR (SWIR, 1.4-3 µm), mid-wavelength IR (MWIR, 3-8 µm), or long-wavelength IR (LWIR, 8-15 µm). Moreover, in some embodiments, a fluorophore described herein has an emission profile overlapping with a wavelength at which water and/or biological tissue has an absorption minimum, such as a wavelength between about 700 nm and about 800 nm or between about 1.25 µm and about 1.35 µm. Additionally, in some cases, a population of ultrasound-switchable fluorophores described herein comprise fluorophores having differing emission profiles for purposes of multiplexed imaging. For example, in some cases, a first fluorophore of the population can emit in the NIR and a second fluorophore of the population can emit in the visible region of the electromagnetic spectrum.

In some embodiments, different populations of ultrasound-switchable fluorophores described herein comprise different fluorophores having different emission profiles for purposes of multiplexed imaging. For example, an emission profile of a first population of ultrasound switchable fluorophores having a first fluorophore can be between about 680 nm and about 710 nm, and the emission profile of a second population of ultrasound switchable fluorophores having a second fluorophore can be between about 740 nm and about 770 nm. In embodiments having a third population of ultrasound switchable fluorophores having a third fluorophore, the emission profile of a third fluorophore can be >840 nm. Moreover, this general principle can be applied to embodiments where n populations of ultrasound switchable fluorophores having n fluorophores are used. In this manner, multiplexed imaging can be achieved.

In addition, a targeting ultrasound-switchable fluorophore described herein comprises a targeting moiety. A "targeting moiety", for reference purposes herein, comprises a molecule having a physical or chemical binding affinity for a target element present in the environment. In cases where the environment is biological or phantom biological, the targeting moiety can be an antibody with specificity to a biomarker present in the environment. For example, the antibodies can have specificity to angiogenic biomarkers, such as non-limiting examples of vascular endothelial growth factor receptor (VEGFR), integrin, CD105, P-selectin, or any other angiogenic biomarkers known to those of ordinary skill in the art. In other instances, the targeting moiety can be a small molecule, polysaccharide, polypeptide, or any other molecule known to bind to a target element present in a biological environment. In some embodiments, the targeting moiety reversibly binds to the target element. In other embodiments, the targeting moiety irreversibly binds to the target element. In some cases, for instance, the targeting moiety is attached to a targeting ultrasound-switchable fluorophore using one or more of a carbodiimide, maleimide, or biotin-streptavidin coupling scheme, as seen for example in FIG. 8. Moreover, any other coupling scheme not inconsistent with the objectives of the current disclosure can be used to attach a targeting moiety to an ultrasound-switchable fluorophore. It is to be understood that in embodiments where n targeting ultrasound-switchable fluorophores are used, each targeting ultrasound fluorophore can have a different targeting moiety.

Further, the non-targeting ultrasound-switchable fluorophore described herein comprises a non-targeting moiety. A "non-targeting moiety", for reference purposes herein, comprises a molecule exhibiting similar physicochemical behavior in the environment as the targeting moiety, but lacking a physical or chemical binding affinity for the target element. Stated differently, the non-targeting moiety is a negative control for the targeting moiety. For example, when the targeting moiety is an antibody with specificity to a biomarker present in the environment, the non-targeting moiety can be an isotype-matched control antibody that lacks specificity to the biomarker, but exhibits similar physicochemical behavior in the environment. In some embodiments, the non-targeting ultrasound-switchable fluorophore can be prepared without any non-targeting moiety. Instead, the ultrasound-switchable fluorophore itself can be used as a negative control to the targeting ultrasound-switchable fluorophore. In some embodiments, the non-targeting moiety is attached to a non-targeting ultrasound-switchable fluorophore using one or more of a carbodiimide, maleimide, or biotin-streptavidin coupling scheme, as seen for example in FIG. 8. Moreover, any other coupling scheme not inconsistent with the objectives of the current disclosure can be used to attach a non-targeting moiety to an ultrasound-switchable fluorophore.

Methods described herein also comprise exposing an environment, such as a biological environment, to one or more ultrasound beams to create an activation region within the environment. The ultrasound beam can have any ultrasound frequency not inconsistent with the objectives of the current disclosure. In some embodiments, an ultrasound beam comprises an oscillating sound pressure wave with a frequency of greater than about 20 kHz or greater than about 2 MHz. In some cases, an ultrasound beam described herein has a frequency of up to about 5 GHz or up to about 3 GHz. In some embodiments, an ultrasound beam has a frequency between about 20 kHz and about 5 GHz, between about 50 kHz and about 1 GHz, between about 500 kHz and about 4 GHz, between about 1 MHz and about 5 GHz, between about 2 MHz and about 20 MHz, between about 2 MHz and about 10 MHz, between about 5 MHz and about 200 MHz, between about 5 MHz and about 15 MHz, between about 200 MHz and about 1 GHz, between about 500 MHz and about 5 GHz, or between about 1 GHz and about 5 GHz.

In addition, an ultrasound beam can have any power not inconsistent with the objectives of the current disclosure. In some embodiments, for instance, an ultrasound beam has a power between about 0.1 W/cm$^2$ and about 10 W/cm$^2$, between about 0.1 W/cm$^2$ and about 5 W/cm$^2$, between about 0.5 W/cm$^2$ and about 5 W/cm$^2$, between about 1 W/cm$^2$ and about 10 W/cm$^2$, or between about 1 W/cm$^2$ and about 5 W/cm$^2$. In other cases, an ultrasound beam has a power between about 100 W/cm$^2$ and about 5000 W/cm$^2$, or between about 100 W/cm$^2$ and about 3000 W/cm$^2$. In some cases, the use of an ultrasound beam having a high power, such as a power described herein, can result in the generation of non-linear effects within the activation region. Moreover, in some embodiments, the effective size of the activation region can be reduced in this manner, leading to improved imaging resolution.

An environment can be exposed to an ultrasound beam in any manner not inconsistent with the objectives of the current disclosure. For example, in some embodiments, a biological environment is exposed to an ultrasound beam described herein for only a limited duration. In some cases, for instance, the ultrasound beam is provided to the environment for less than about 1 second or less than about 500 ms. In some embodiments, the ultrasound beam is provided to the environment for less than about 300 ms, less than about 100 ms, less than about 50 ms, or less than about 10 ms. In some cases, the ultrasound beam is provided to the environment for about 1 ms to about 1 second, about 1 ms to about 500 ms, about 1 ms to about 300 ms, about 1 ms to about 100 ms, about 1 ms to about 50 ms, about 1 ms to about 10 ms, about 10 ms to about 300 ms, about 10 ms to about 100 ms, about 10 ms to about 50 ms, or about 50 ms to about 100 ms. The use of short exposure times of a biological environment to an ultrasound beam, in some embodiments, can permit the time-gating of fluorescence signals, such that a desired USF signal can be temporally separated from one or more undesired or non-analyte fluorescence signals, such as a tissue autofluorescence signal or a signal from a randomly switched-on fluorophore.

Moreover, the ultrasound beam can be a continuous wave beam or a pulsed or modulated beam. The use of a modulated or pulsed ultrasound beam, in some embodiments, can further improve the signal to noise ratio (SNR) of a method described herein by permitting frequency-gated detection of the USF signal. For example, in some cases, a pulsed or modulated ultrasound beam provides an ultrasound exposure having a specific frequency or modulation. As a result, the corresponding USF signal can also exhibit the same specific frequency or modulation. Thus, in some such cases, a lock-in amplifier is used to increase the sensitivity of the detector to the specific frequency or modulation, thus increasing the overall sensitivity and SNR of the method. The use of a modulated ultrasound beam can also improve the temperature resolution of a method described herein, as described further hereinbelow.

In some embodiments of methods described herein, a single ultrasound beam is directed toward the environment using a single ultrasound transducer, such as a high intensity focused ultrasound (HIFU) transducer. In other instances, a plurality of ultrasound beams is directed toward the environment using a plurality of ultrasound transducers. Moreover, in some cases, a first ultrasound beam is directed toward the environment at a first angle and/or from a first direction, and a second ultrasound beam is directed toward the environment at a second angle and/or from a second direction differing from the first angle and/or direction. In some embodiments, for instance, the first and second directions are orthogonal or substantially orthogonal directions, such as directions separated by 80 to 100 degrees. In other cases, the directions are separated by less than 80 degrees or more than 100 degrees. Further, if desired, additional ultrasound beams may also be directed toward the environment from additional directions or at additional angles. In such cases, the focal zones of the beams can overlap or intersect with one another to form an activation region at the intersection of the beams. In this manner, an activation region can have a smaller volume or cross section than the focal zone or cross section of a single ultrasound beam used to generate the activation region, thereby improving imaging resolution. In some cases, for instance, the activation region has a lateral dimension and/or an axial dimension of less than about 2 mm, less than 1.5 mm, or less than about 1 mm. In some embodiments, the activation region has a lateral dimension and/or an axial dimension of less than about 700 µm or less than about 500 µm. In some embodiments, the activation region has a lateral dimension and/or an axial dimension of about 300 µm to about 2 mm, about 400 µm to about 1.5 mm, about 400 µm to about 1 mm, about 400 µm to about 700 µm, or about 400 µm to about 500 µm. In some cases, the lateral and axial dimensions both have a size recited herein, including a size below about 1 mm or below about 700 µm. Moreover, in some embodiments, the lateral and axial dimensions of the activation region are different, thereby providing a relatively anisotropic activation region. Alternatively, in other instances, the lateral and axial dimensions are substantially the same, thereby providing a relatively "square" or isotropic activation region.

An "activation region," for reference purposes herein, comprises a region of the environment in which ultrasound-switchable fluorophores described herein are or can be switched from an off state to an on state. For example, in some cases, an activation region comprises a region of high temperature compared to other portions of the environment. Moreover, as described further herein, the size, shape, and/or other properties of the activation region can be determined by the number and/or power of the one or more ultrasound beams used to form the activation region. In some cases, for instance, the size and shape of an activation region is defined by the focal zone of a single ultrasound beam. In other cases, an activation region is defined by the overlap of the focal zones of a plurality of ultrasound beams.

A fluorophore described herein can be disposed within an activation region in any manner not inconsistent with the objectives of the current disclosure. In some cases, a fluorophore enters or is disposed within an activation region of an environment by diffusing into the activation region from an adjacent area of the environment. In other instances, an activation region is created within a specific location within an environment where it is known that a fluorophore or population of fluorophores is likely to be found or may be found. For example, in some embodiments, an ultrasound beam described herein is raster scanned across or within an environment, thereby producing a plurality of activation regions in different locations within the environment in a sequential manner.

Methods described herein also comprise exposing an environment to a beam of electromagnetic radiation and/or exciting at least one fluorophore in an on state with a beam of electromagnetic radiation. A fluorophore can be excited with a beam of electromagnetic radiation in any manner not inconsistent with the objectives of the current disclosure. In some embodiments, for instance, a fluorophore is excited using a laser excitation source such as a diode laser. In other instances, a fluorophore is excited using one or more light emitting diodes (LEDs) or a broadband excitation source. Moreover, an excitation source described herein can provide any wavelength of light not inconsistent with the objectives of the current disclosure. In some embodiments, a fluorophore described herein is excited with a beam of electromagnetic radiation comprising visible light, NIR light, or IR light. In other cases, the beam of electromagnetic radiation comprises ultraviolet (UV) light. In some embodiments, a fluorophore described herein is excited with a beam of electromagnetic radiation comprising a wavelength maximum of approximately 671 nm, 730 nm, or 810 nm.

Methods described herein also comprise detecting a photoluminescence signal or other light emitted within an environment or within a specific location within an environment. In some embodiments, for instance, a method comprises detecting light emitted by at least one ultrasound-switchable fluorophore. Light emitted by the fluorophore can be detected in any manner not inconsistent with the objectives of the current disclosure. In some embodiments, for example, detecting light emitted by at least one fluorophore in an on state comprises detecting the light in a time-gated or frequency-gated manner, including a time-gated manner or frequency-gated manner described herein. In some cases, the light emitted by the at least one fluorophore in the on state is detected after a time delay that is longer than the fluorescence lifetime of the fluorophore in the off state or longer than the fluorescence lifetime of another species present in the biological environment. For example, in some embodiments, the light emitted by the at least one fluorophore in the on state is detected after a time delay that is longer than the autofluorescence lifetime of a non-fluorophore species present in the biological environment, such as the autofluorescence lifetime of tissue, which may be up to about 4 ns or up to about 5 ns.

In addition, the photoluminescence signals of a method described herein can be detected using any detector configuration not inconsistent with the objectives of the current disclosure. In some embodiments, for instance, a photoluminescence signal is detected using a detector comprising a plurality of optical fiber collectors coupled to a camera or photon counter, such as a charge coupled device (CCD) or a photomultiplier tube (PMT). Further, in some cases, the optical fiber collectors are spatially distributed around the environment or around a detection surface of the environment (such as skin or another exterior surface of the environment). Any desired number of optical fiber collectors can be used. In some embodiments, up to 30, up to 20, or up to 10 optical fiber collectors are used. In some cases, 4-30, 4-20, 6-30, 6-20, 8-30, 8-20, 10-30, or 10-20 optical fiber collectors are used. Other configurations are also possible.

Additionally, in some cases, a plurality of photoluminescence signals at a plurality of locations within an environment is detected by raster scanning the environment. Such raster scanning can include raster scanning of one or more ultrasound beams across or within the environment, such that the ultrasound beam sequentially generates a series of activation regions at different locations within the environment. It is also possible, in some instances, to move or scan a detector described herein from location to location within the environment. Moving or scanning a detector in such a manner can increase the detection area of the method. In other cases, a two-dimensional detector such as a charge-coupled device (CCD) image sensor or camera is used to detect photoluminescence signals at a plurality of locations simultaneously.

Methods of imaging described herein, in some embodiments specifically described below in the examples, also comprise determining a photoluminescence property of the population of non-targeting fluorophores from the photoluminescence signal emitted by the population of non-targeting fluorophores. For example, the photoluminescence property can include an emission intensity, a location in the environment where the photoluminescence signal originated, an emission color, or any other photoluminescence property. Photoluminescence properties can be determined by any method not inconsistent with this disclosure. In some cases, the photoluminescence property is determined using a photoluminescence detector that measures intensity and/or geographic location of the photoluminescence signal emitted by the population of non-targeting fluorophores.

Methods of imaging, described specifically below in the examples, can also comprise using the determined photoluminescence property of the population of the non-targeting fluorophores to deconvolute a photoluminescence signal emitted by the population of targeting fluorophores to determine what proportion of the population of targeting fluorophores are bound and unbound to a target binding element in the environment. For example, an emission intensity and/or geographic location of the photoluminescence signal emitted by the population of targeting fluorophores can be mathematically deconvoluted from the emission intensity and/or geographic location of the photoluminescence signal of the non-targeting fluorophores in a manner described in Table 2 below. Additionally, the photoluminescence signal of emitted by the population of targeting fluorophores can be mathematically deconvoluted by any photoluminescence property of the population of non-targeting fluorophores in any manner not inconsistent with this disclosure.

Additionally, in some embodiments of a method described herein and specifically described below in the examples, the determined photoluminescence property of the population of non-targeting fluorophores can be used to deconvolute a photoluminescence signal emitted by the population of n targeting fluorophores to determine what proportion of the population of n targeting fluorophores are bound and unbound to a target binding element in the environment. The method in which the photoluminescence signal is deconvoluted can be in any manner not inconsistent with this disclosure. In some cases, an emission intensity and/or geographic location of the photoluminescence signal emitted by the population of n targeting fluorophores can be mathematically deconvoluted from the emission intensity and/or geographic location of the photoluminescence signal of the non-targeting fluorophores in a manner described in Table 2 below.

EXAMPLE 1

Targeting and Non-Targeting Ultrasound Switchable Fluorophores

Targeting and non-targeting ultrasound-switchable fluorophores suitable for use in some embodiments of methods described herein are prepared in a manner described in U.S. Patent Application Publication No. 2015/0309014 to Yuan et al. ("the '014 publication"), which is again incorporated herein in entirety.

Figure 2:
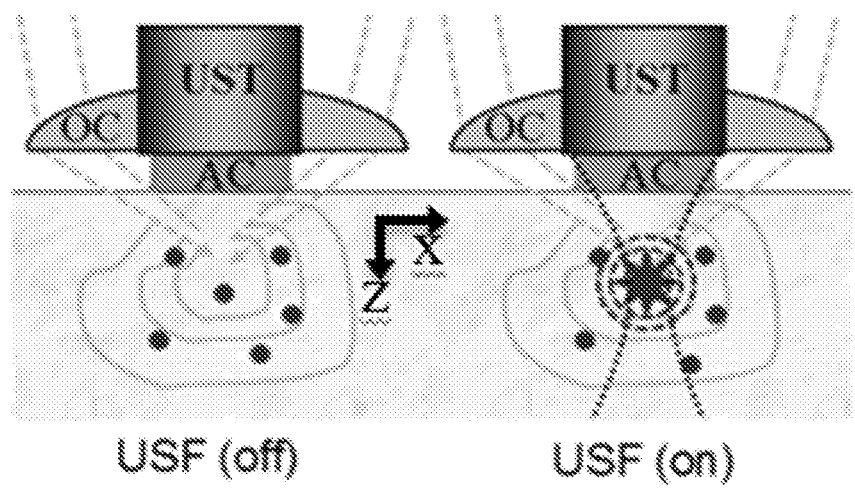
FIG. 2 illustrates schematically steps of a method of forming an activation region.

As described above, this disclosure relies generally on ultrasound fluorescence (USF) imaging. As understood by one of ordinary skill in the art and as described above, USF commonly operates according to the following principles. When an environment-sensitive near infrared (NIR) fluorescent dye (such as ZnPC, ZnPcOB, ADP(CA)$_2$, ICG, among others) is encapsulated into a thermo-sensitive nanoparticle (made by Pluronic F127, F98, F68, among others.), the dye's fluorescence emission exhibits a switch-like function of the temperature (FIG. 1). Briefly, when the temperature is below a threshold (T<$T_{th1}$), the nanoparticle exhibits hydrophilicity and provides a water-rich, polar, and non-viscous microenvironment in which the dye shows very low emission efficiency (so-called OFF). When T is above another threshold (T>$T_{th2}$), the nanoparticle exhibits hydrophobicity and provides a polymer-rich, non-polar, and viscous microenvironment in which the dye shows strong emission (so-called ON). When the transition bandwidth ($T_{BW}=T_{th2}-T_{th1}$) is narrow, the fluorescence intensity appears a switch function as the temperature. The first threshold ($T_{th1}$) is also known as LCST (the lower critical solution temperature of the thermo-sensitive nanoparticles). In USF imaging, the threshold $T_{th1}$ can be controlled slightly above the tissue background temperature ($T_{BG}$) (i.e. $T_{BG}<T_{th1}$) to maintain an OFF state (FIG. 2). For example, $T_{th1}$=39° C. is above $T_{BG}$=37° C. (body temperature). When the focused ultrasound is applied, the tissue temperature (T) at the focus will be increased above the threshold (T>$T_{th1}$) to switch on the fluorophores (FIG. 2). The USF agents outside the focus remain off. A high-resolution USF image can be formed via point-by-point scanning of ultrasound focus.

In USF imaging, NIR excitation light is delivered into centimeters deep tissue via light scattering (see the curves in FIG. 2). When ultrasound is off, no or weak fluorescence is emitted although the excitation light is on (see FIG. 2). When ultrasound is on, the USF contrast agents in the ultrasound focal volume can be switched on to emit fluorescence (see the dashed circles in FIG. 2). The emitted NIR photons can propagate out of the tissues via light scattering (towards all directions). All the ultrasound-induced fluorescence photons are signal and should be collected as many as possible. FIG. 2 shows the cross section of the sample (i.e. on x-z plane).

In USF imaging, only ultrasound-induced fluorescence photons are used as the signal. These photons can be generated only from the region around the ultrasound focus. Thus, the spatial resolution of USF depends on the size of this region. The thermal energy can be confined into the ultrasound focal region when the ultrasound exposure time is shorter enough than the thermal diffusion time (i.e. so-called thermal confinement). Unlike pure ultrasound or photoacoustic imaging (f-number usually >2), USF uses an ultrasound transducer with a small f-number (<1) to reduce the focal size. In addition, USF contrast agents can be switched on only in a region where ultrasound energy is above the switching-on threshold ($T_{th1}$). The existence of this threshold makes the region is usually smaller than the actual size of the ultrasound-induced thermal focus. Lastly, if nonlinear acoustic effect occurs, both lateral and axial focal sizes can further shrink.

NIR region can cover 670-900 nm. Therefore, appropriately selecting NIR fluorophores (for USF contrast agents) with different excitation (Ex) and emission (Em) wavelengths permits multi-color (multiplex) imaging to be conducted. For example, Color-1 can be selected as being from ZnPC with Ex=671 nm and Em=680-710 nm; Color-2 can be from ZnPcOB with Ex=730 nm and Em=740-770 nm; and Color-3 can be from ICG with Ex=810 nm and Em>840 nm (See FIGS. 3A and 3B). Although spectral cross talk may be possible, several strategies can be adopted to minimize or unmix them, as described further hereinbelow. Thus, USF can simultaneously identify multiple targets via multi-colors, which will significantly increase the specificity to the targets (none of CT, MRI, PET and ultrasound has this capability).

Figure 3A:
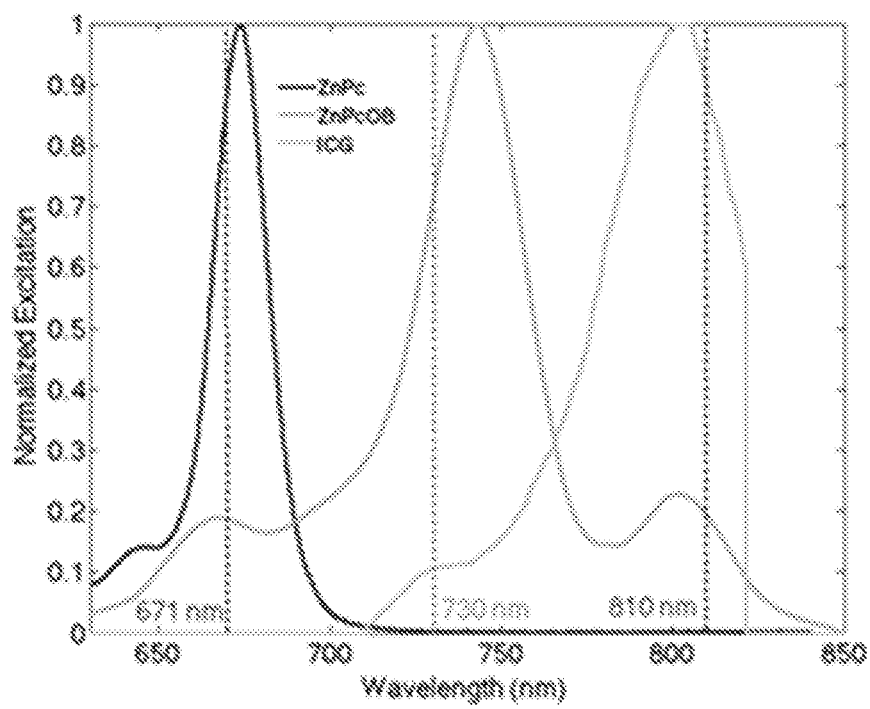
FIG. 3A illustrates a plot of excitation profiles for a series of ultrasound-switchable fluorophores.
Figure 3B:
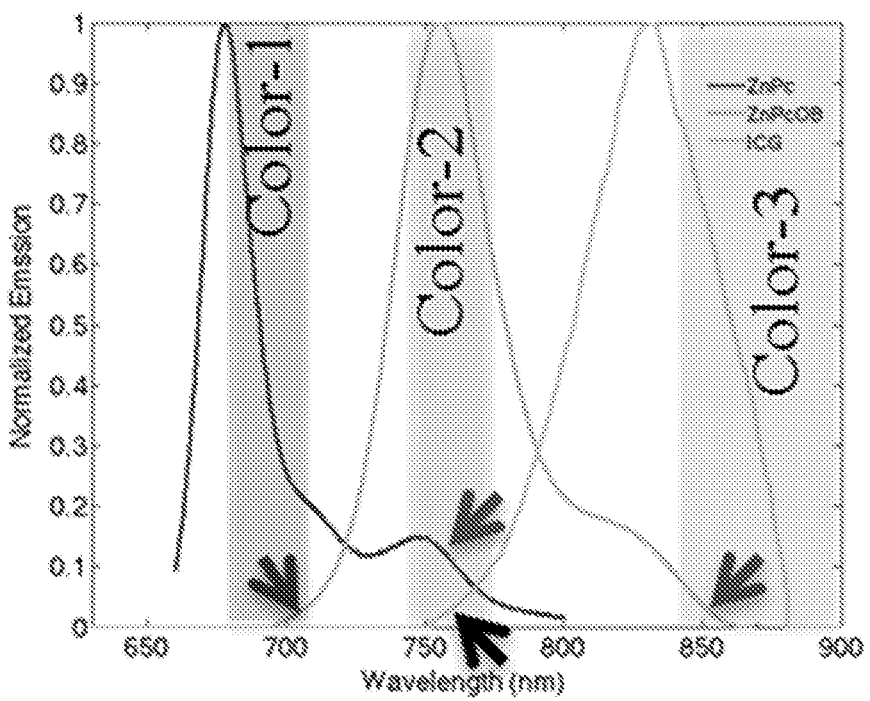
FIG. 3B illustrates a plot of emission profiles for a series of ultrasound-switchable fluorophores.

There are two common types of spectral cross talk. The first one is so-called "one laser excites multiple fluorophores" cross talk, due to the excitation spectrum overlap. For example, when the 671-nm laser is on, it may excite both ZnPc and ZnPcOB (FIG. 3A). This type of cross talk can be reduced or avoided via sequentially turning on each laser-camera pair, as described further hereinabove and hereinbelow. Briefly, the USF system can sequentially turn on each laser-camera pair via an accurate electronic triggering system. For example, the Color-1 channel's camera is triggered ON and will detect the emission mainly from ZnPc. In contrast, the Color-2 and Color-3 channel's cameras are OFF, so the emission from ZnPcOB (excited by the 671-nm laser) will not be detected. Similarly, this rule is true for the other two laser-and-camera pairs.

The second type of cross talk is so-called "spectral bleed-through" cross talk, caused by the emission spectrum overlap. This cross talk can lead to emission leakage from one fluorophore channel to another (see the arrows in FIG. 3B). For example, when the 671-nm laser is on and possibly excites both ZnPc (strongly) and ZnPcOB (weakly), a small part of the emission from ZnPcOB (belongs to Color-2) may leak to the Color-1 channel's camera (it is the only camera that is turned on at this moment) because of the emission spectral overlap. This type of cross talk can be minimized via carefully selected emission filters and excitation light wavelengths. This type of cross talk may also be minimized or eliminated via a signal processing method, as described further herein. Also, if needed, any unavoided spectral leakage can be quantified prior to temperature measurement by using tissue phantoms and/or in vivo tissues, and then taken into account in further signal processing.

Figure 8:
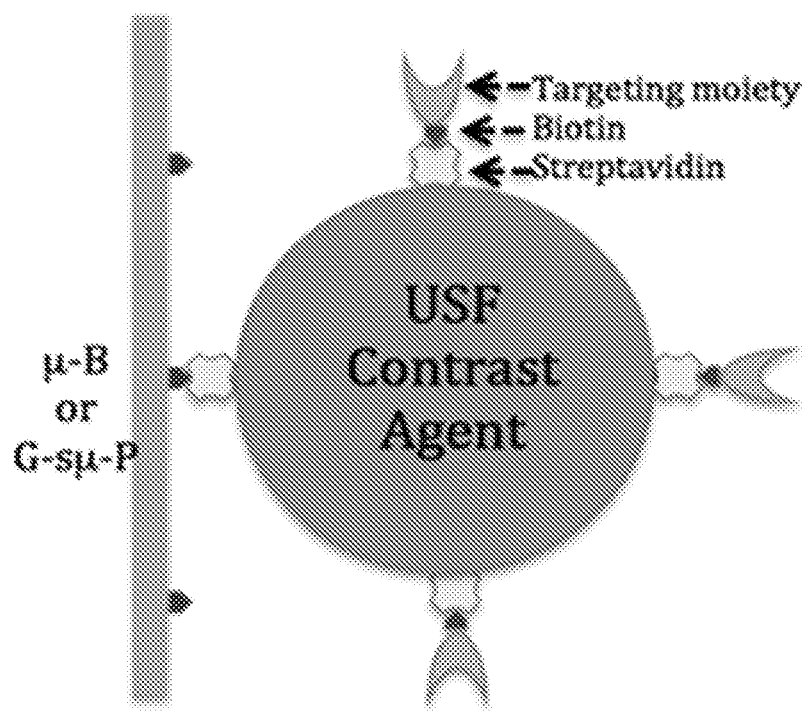
FIG. 8 illustrates an exemplary USF contrast agent bound to a microbubble and to a targeting moiety through biotin-streptavidin linkages.

Additionally, gas-filled micro-particles, such as the above described microbubbles, can generate a short but high temperature pulse in and around the particle surface when the microbubble is irradiated with an ultrasound pulse at diagnostic intensity level. This short temperature pulse spatially decays very fast (only ~0.2° C. left at a distance of 1 micron away from the bubble surface). In USF imaging, tissue overheating caused by microbubbles is minimalized from this fast temperature decay. However, this microscopic heating principle is very useful for heating ultrasound switchable fluorophores, because ultrasound switchable fluorophores are small nanoparticles that can be attached on the microbubble's surface. For example, ultrasound switchable fluorophores (e.g. USF contrast agents) can be attached to a surface of a microbubble through a biotin/streptavidin linkage (see FIG. 8), or other common linkages. As seen in FIG. 8, biotin has been incorporated onto the surface of the microbubble μ-B or G-sμ-P, and streptavidin has been incorporated onto to the surface of the USF contrast agent.

A highly ultrasound-absorbing polymer, biodegradable polyurethane with pendent carboxyl groups (PU—COOH), can alternatively be used instead of the microbubbles. These ultrasound-absorbing polyurethanes make relatively rigid gas-filled sub-micro-particles (~700 nm in diameter). These relatively rigid particles are much more stable than microbubbles, and their acoustic attenuation is significantly reduced because of smaller size (but still stay in blood vessels). More importantly, these particles can be efficiently heated for USF imaging because of ~22 times higher in acoustic absorption, ~2.3 times lower in specific heat capacity, ~3 time lower in thermal conductivity compared with soft tissue. Similar to the microbubbles, biotin can be incorporated onto the surface of the ultrasound-absorbing polyurethanes, and the USF contrast agents can be attached using the streptavidin linkage.

Targeting and non-targeting moieties were attached to surfaces of different populations of ultrasound-switchable fluorophores having different excitation and emission wavelength profiles, such as ZnPc, ZnPcOB, or ICG. As shown in FIG. 8, each of the targeting and non-targeting moieties were attached to their respective ultrasound-switchable fluorophores via a biotin/streptavidin linkage. In one embodiment, an anti-mouse VEGFR2 monoclonal antibody and an isotype-matched control antibody were respectively adopted as the targeting moiety and non-targeting (negative control) moiety, and attached to two ultrasound-switchable fluorophores having different excitation and emission wavelength profiles. In another embodiment, an $α_vβ_3$ peptide c(RGDfK) and an modified peptide c(RADfK) were respectively adopted as the targeting moiety and non-targeting (negative control) moiety, and attached to two ultrasound-switchable fluorophores having different excitation and emission wavelength profiles.

EXAMPLE 2

USF Thermometry Systems

USF thermometry systems suitable for use in some embodiments of methods described herein are provided as follows. The systems generally include optical, electronic and acoustic subsystems. The time to fire a laser (excitation) pulse and the time to trigger its corresponding camera is accurately controlled. Also, the optical and electronic systems are synchronized with a HIFU therapeutic system for simultaneous thermal treatment and temperature monitoring.

Figure 4:
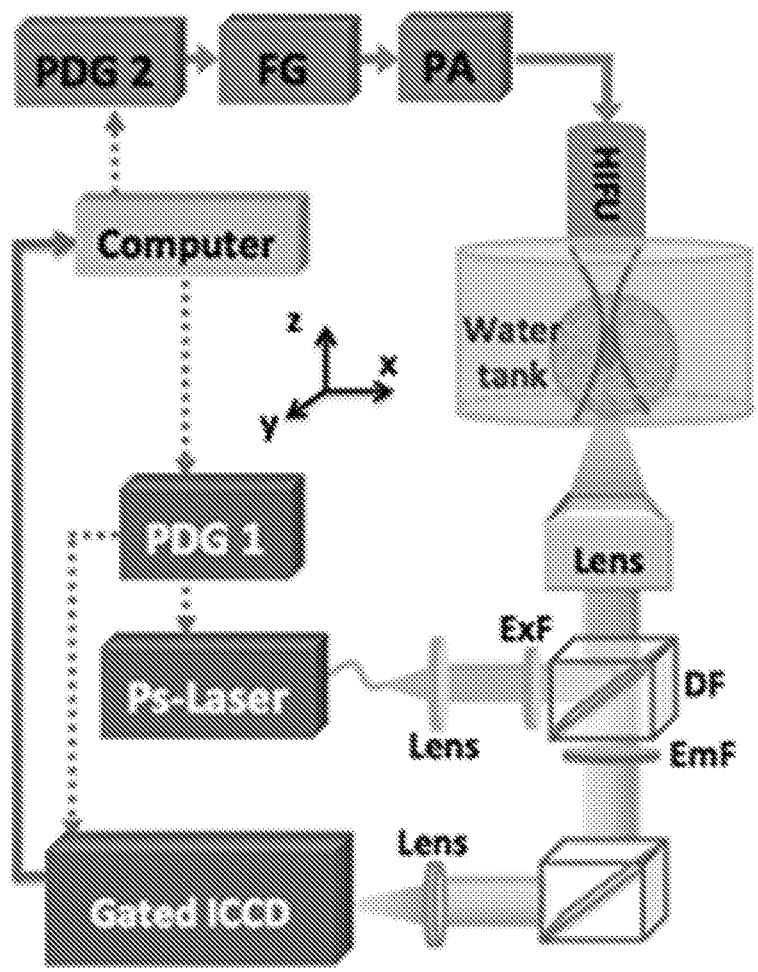
FIG. 4 illustrates schematically a time-domain USF imaging system.

One so called time-domain USF imaging system includes (1) a gated intensified charge coupled device (ICCD) camera. The intensified nature of the ICCD is obtained from an optical amplifier whose gain can be electronically and fast gated with a response time of ps or ns, and a CCD camera with a response time of ms. The system can further include (2) a fast and gated photomultiplier tube (PMT, whose gain can be fast gated with a response time of ps or ns). The system diagram is shown in FIG. 4. The components represent, inter alia, HIFU treatment system components, including a HIFU treatment transducer (2.5 MHz, Sonic Concepts, H-108), a RF power amplifier (PA), and a function generator (FG). A pico-second (ps) pulsed laser is used as the excitation light source. Other components represent the ICCD and PMT based optical detection systems. A pulser-delay generator (PDG) with multi-channels is used to control the time sequence of the entire system. A computer is adopted to acquire the data. To measure the HIFU-induced temperature increase inside the tissue sample, a small thermocouple (with a junction size of 25 μm to avoid possible viscous heating) is attached inside a micro-tube that is filled with USF contrast agent solution. The micro-tube is embedded inside the tissue sample.

Figure 5:
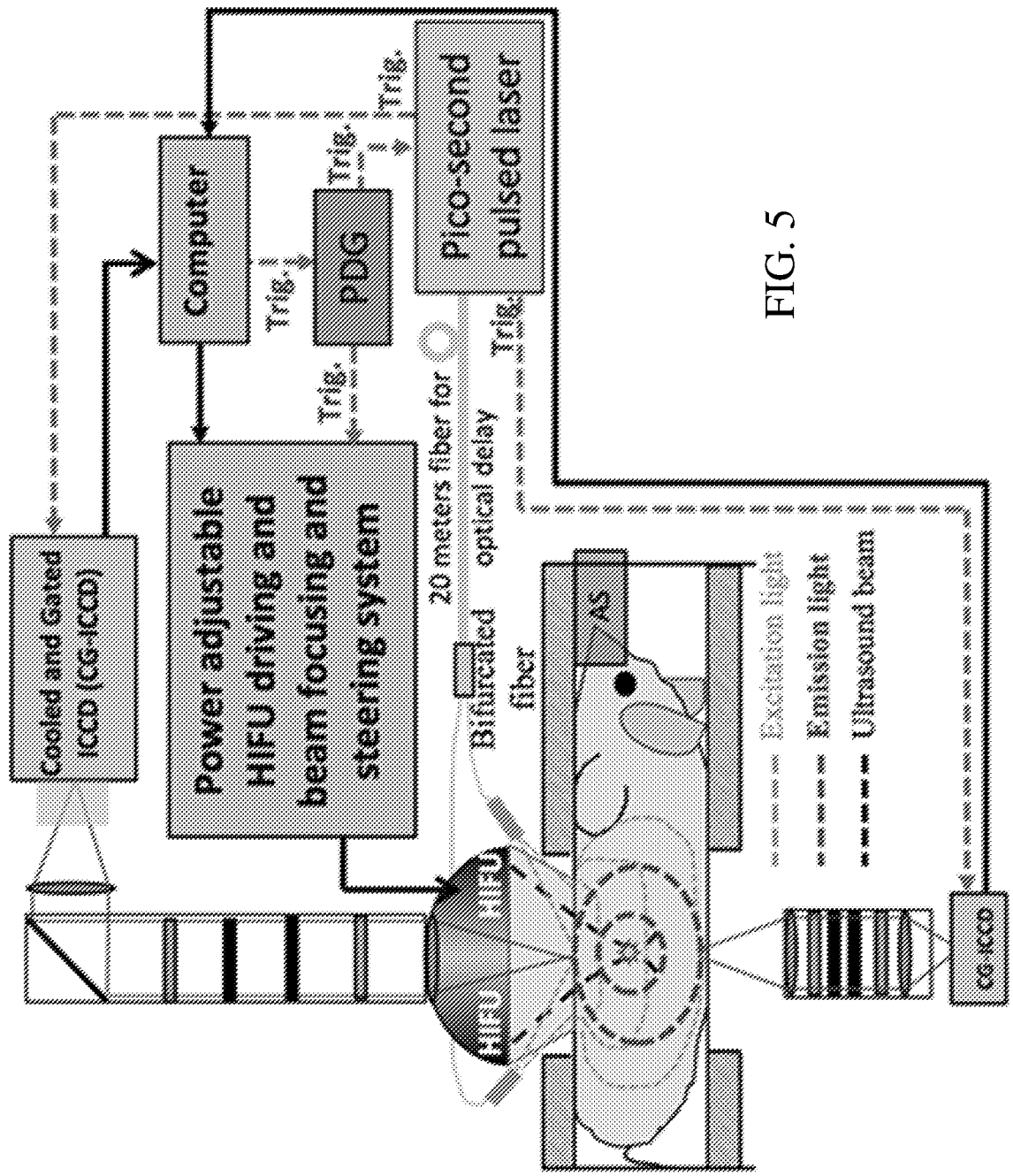
FIG. 5 illustrates schematically an in vivo USF imaging system.

Another USF system is illustrated in FIG. 5. As illustrated in FIG. 5, this system is specifically designed for use with small animals (such as a mouse or rat). Compared with the system of FIG. 4, the system of FIG. 5 includes the following notable components: (1) an animal holding system; (2) a tightly focused ultrasound transducer array (4.5 MHz, H-178, Sonic Concepts); (3) a single optical fiber bundle; and (4) multiple gated and intensified CCD (ICCD) cameras. The tightly focused ultrasound transducer array replaces time-consuming mechanical scanning of other USF systems, and permits fast electronic scanning that does not require waiting for tissue cooling down at one location before scanning to the next location. The single optical fiber bundle can, for example, have an effective diameter of ~1.5 mm to collect USF photons. The use of multiple gated ICCD cameras will increase USF imaging sensitivity by enlarging the photon collection area, because USF photons propagate spherically from deep tissue. For example, multiple (2 or 3) gated ICCD cameras are positioned at different positions: one on the top of the HIFU transducer array though a central hole, and another one (or two) at the bottom (or two sides). The use of multiple gated ICCD also permits collection of three colored USF photons in one ultrasound exposure, increasing the imaging speed and while simultaneously imaging three colored agents (e.g. fluorophores).

EXAMPLE 3

Methods of Differentiating Bound from Unbound Contrast Agents

Methods of USF imaging according to some embodiments described herein were carried out as follows. As described above, the method can increase the specificity of USF imaging by differentiating specifically bound contrast agents from unbound contrast agents, and resolving binding dynamics of contrast agents to specific biomarkers using USD multi-color imaging. Two angiogenic biomarkers are chosen as targets, VEGFR2 or $\alpha_v\beta_3$, due to overexpression in human cancers.

When solely imaging VEGFR2, an anti-mouse VEGFR2 monoclonal antibody and an isotype-matched control antibody were respectively adopted as the targeting and non-targeting (negative control) moieties (see Table 1 below). The VEGFR2 targeting ultrasound-switchable fluorophore (USF$_V$) and the VEGFR2 negative control non-targeting ultrasound-switchable fluorophore (USF$_{VC}$) were simultaneously imaged via Color-1 and Color-3, respectively.

Similarly, when solely imaging $\alpha_v\beta_3$, peptides, c(RGDfK) and c(RADfK) were respectively used as the targeting and non-targeting (negative control) moieties (see Table 1 below). The $\alpha_v\beta_3$ targeting ultrasound-switchable fluorophore (USF$_{ab}$) and the $\alpha_v\beta_3$ negative control non-targeting ultrasound-switchable fluorophore (USF$_{abC}$) were simultaneously imaged via Color-2 and Color-3, respectively.

When simultaneously imaging both VEGFR2 and $\alpha_v\beta_3$, USF$_V$ and USF$_{ab}$ were used, and a non-targeting ultrasound-switchable fluorophore without any targeting moieties (USF$_{non}$) was used as a common negative control. The three agents were simultaneously imaged via Color-1, -2 and -3, respectively.

TABLE 1

Summary of USF Multiplex Imaging Strategy

| | | Molecular Targets | | | | | |
|---|---|---|---|---|---|---|---|
| | VEGFR2 | | $\alpha_v\beta_3$ | | VEGFR2 and $\alpha_v\beta_3$ | | |
| | Targeted agent | Negative control | Targeted agent | Negative control | Targeted agent for VEGFR2 | Targeted agent for $\alpha_v\beta_3$ | Negative control for both |
| Targeting moiety | Anti-mouse VEGFR2 monoclonal antibody | Isotype-matched control antibody (or no any antibody) | c(R DfK) peptide | c(RADfK) peptide (or no any peptide) | Anti-mouse VEGFR2 monoclonal antibody | c(RGDfK) peptide | No targeting moiety |
| Notation of agents | USF$_V$ | USF$_{VC}$ | USF$_{ab}$ | USF$_{abC}$ | USF$_V$ | USF$_{ab}$ | USF$_{non}$ |
| Color | Color-1 | Color-3 | Color-2 | Color-3 | Color-1 | Color-2 | Color-3 |
| $\lambda_{ex}$; | Ex: 671 nm | Ex: 810 nm | Ex: 730 nm | Ex: 810 nm | Ex: 671 nm | Ex: 730 nm | Ex: 810 nm |
| $\lambda_{em}$ | Em: 680-710 nm | Em: >840 nm | Em: 740-770 nm | Em: >840 nm | Em: 680-710 nm | Em: 740-770 nm | Em: >840 nm |

The rationale of imaging the binding dynamics of the targeting contrast agents assumes that unbound targeting ultrasound-switchable fluorophores ($USF_V$) behave similarly to the non-targeting ultrasound-switchable fluorophore ($USF_{VC}$) negative control agent. This is because (1) physiochemically the two fluorophores are quite similar; (2) their hydrodynamic behavior in blood should be similar; and (3) there are no forces in body to separate them.

Figure 6:
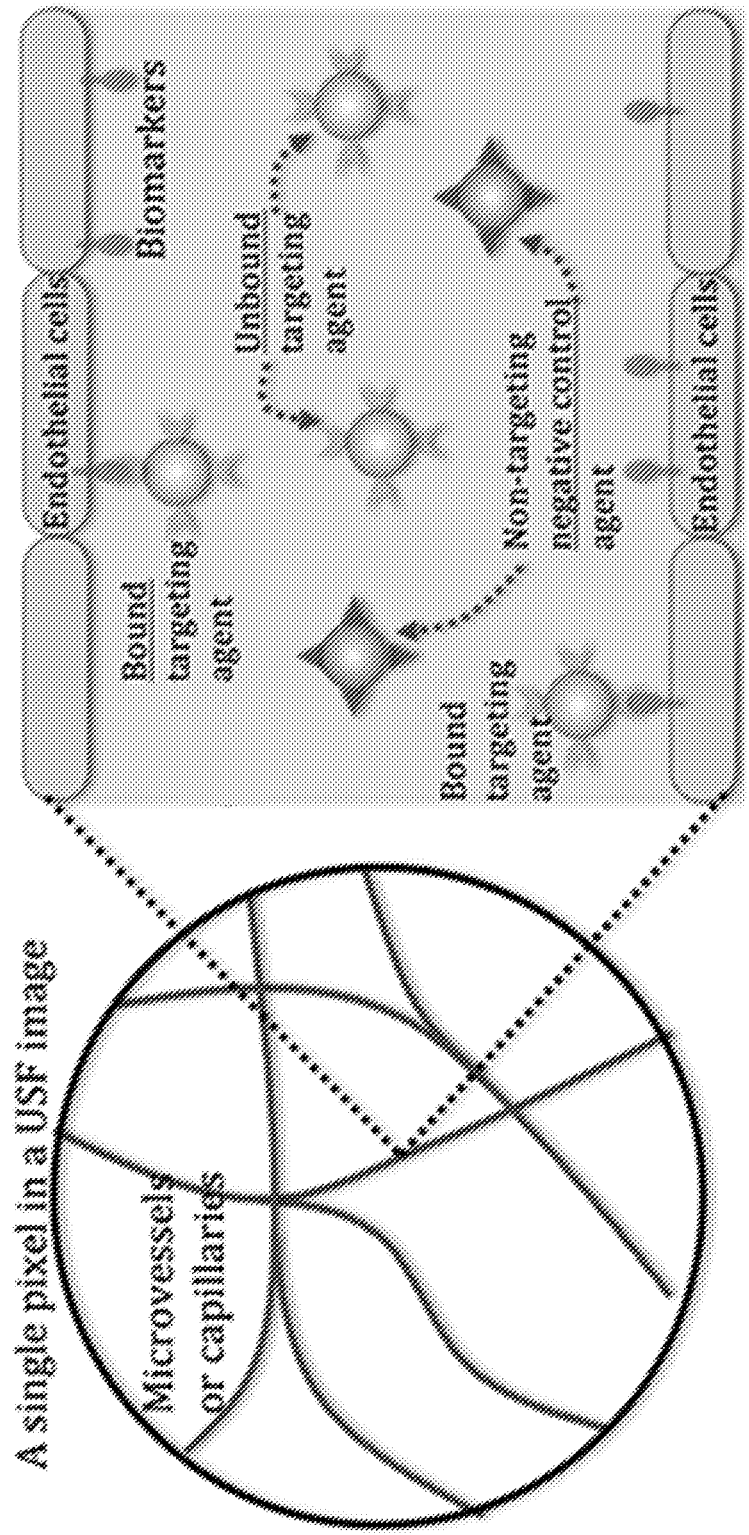
FIG. 6 illustrates a two-compartment model of a vascular bio-tissue with bound and unbound targeting ultrasound-switchable fluorophores.
Figure 7:
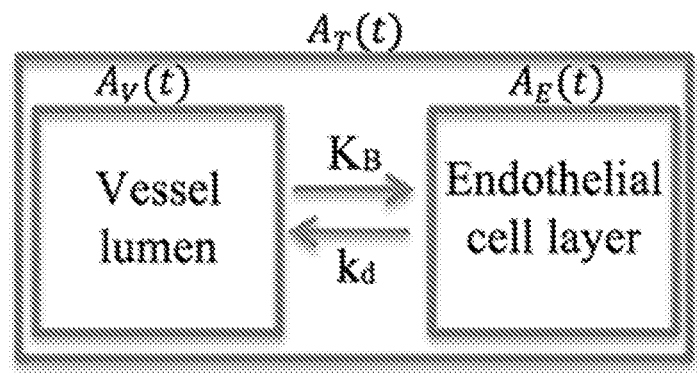
FIG. 7 illustrates a block diagram of the binding kinetics of the targeting ultrasound-switchable fluorophores in the two compartment model of FIG. 6.

Using the VEGFR2 targeting ultrasound-switchable fluorophore as an example, with other types of targeting ultrasound-switchable fluorophores being similar mutatis mutandis, a two-compartment model frequently used in contrast-enhanced CT angiography is modified to (1) normalize all signals to avoid the effects of any unknown factors; and (2) incorporate multi-colors. A cluster of microvessels is included in one pixel (or voxel) of a USF image (FIG. 6A). Thus, these vessels are considered as a whole. The vessel space in this pixel can be divided into two compartments: vessel lumen (V) and endothelial cell layer (E) (FIGS. 6B and 7).

TABLE 2

Related Equations of the Two-Compartment Model

Eq. (1) $dA_E^{\lambda_1}(t)/dt = K_{BA_V}^{\lambda_1}(t) - k_{dA_E}^{\lambda_1}(t)$;
Eq. (2) $A_T^{\lambda_1}(t) = A_E^{\lambda_1}(t) + A_V^{\lambda_1}(t)$;
Eq. (3) $A_E^{\lambda_1}(t) = K_B \int_0^t A_V^{\lambda_1}(u) e^{-k_d(t-u)} du$, $(A_E^{\lambda_1}(0) = 0)$;
Eq. (4) $A_V^{\lambda_1}(t) = C A_V^{\lambda_3}(t)$
Eq. (5) $A_{T-Norm}^{\lambda_1}(t) = D[K_B \int_0^t A_{V-Norm}^{\lambda_3}(u) e^{-k_d(t-u)} du + A_{V-Norm}^{\lambda_3}(t)]$
Eq. (6) $A_{E-pct}^{\lambda_1}(t) = DK_B \int_0^t A_{V-Norm}^{\lambda_3}(t) e^{-k_d(t-u)} du$, where $A_{E-pct}^{\lambda_1}(t) = A_E^{\lambda_1}(t)/\max(A_T^{\lambda_1}(t))$;
Eq. (7) $\tau/\tau_0 = \int_0^\infty A_{E-pct}^{\lambda_1}(t) dt / \int_0^\infty A_{T-Norm}^{\lambda_1}(t) dt$ The amount of each type of agent in each compartment ($A_V(t)$ in V or $A_E(t)$ in E) is connected by a dynamic rate equation (Eq. 1 in Table 2) via a binding rate constant ($K_B$) and a detaching rate constant ($k_d$) (1/second) (see FIG. 7). The solution of $A_E(t)$ in Eq. 1 is given in Eq. 3. In practice, the total amount of the agent ($A_T(t) = A_E(t) + A_V(t)$, (Eq. 2) is measurable because it is linearly proposal to the USF signal from that pixel (similar to CT). Because $A_T(t)$ is measured at Color-1, it is denoted as $A_T^{\lambda_1}(t)$ ($\lambda_1$ means Color-1). Another measurable variable is the USF signal from the negative control contrast agents at Color-3 (denoted as $A_V^{\lambda_3}(t)$). The following relationship, $A_V^{\lambda_1}(t) = C A_V^{\lambda_3}(t)$, (Eq. 4) is established based on the previous assumption, where C is an unknown and non-dimensional constant. Thus, Eq. 5 is obtained by inserting Eqs. 3 and 4 into Eq. 2, where $A_{T-Norm}^{80\ 1}(t)$ and $A_{V-Norm}^{\lambda_3}(t)$ are normalized signals of $A_T^{\lambda_1}(t)$ and $A_V^{\lambda_3}(t)$; and D is a new unknown and non-dimensional constant. Fitting the experimentally measured $A_{T-Norm}^{\lambda_1}(t)$ and $A_{V-Norm}^{\lambda_3}(t)$ to Eq. 5, the values of $K_B$, $k_d$ and D are determined. Then, inserting these values and $A_{V-Norm}^{\lambda_3}(t)$ into Eq. 6, the normalized binding dynamic function $A_{E-pct}^{\lambda_1}(t)$ (linearly equivalent to $A_E^{\lambda_1}(t)$) is determined. The accumulated time (i.e. lifetime) of all the bound Color-1 agents can be calculated as $\tau = \int_0^\infty A_{E-pct}^{\lambda_1}(t) dt$. The accumulated time of the total Color-1 agents (including bound and unbound agents) residing in that pixel can be calculated as $\tau_0 = \int_0^\infty A_{T-Norm}^{\lambda_1}(t) dt$. The ratio of $\tau/\tau_0$ represents the relative lifetime of the bound Color-1 agents compared with the lifetime of the total Color-1 agents in a single USF pixel.

When USF is spatially scanned, three images about $K_B(r)$, $k_d(r)$ and $\tau(r)/\tau_0(r)$ and one video $A_{E-pct}^{\lambda_1}(r,t)$ can be acquired. $K_B(r)$ and $k_d(r)$ indicate how fast the agents bind and detach, respectively. $A_{E-pct}^{\lambda_1}(r, t)$ represents the how dynamically the agents bind and detach. $\tau(r)/\tau_0(r)$ reflects that how many and how long the bound agents stay in each pixel relative to the total targeting agents. These mesoscopically averaged parameters in each pixel closely correlate with the microscopic parameters of the angiogenic blood vessels, such as the biomarker's local concentration (or amount), binding strength of the targeting contrast agent to the biomarker, and others, which cannot be in vivo detected by other technologies or conventional molecular imaging.

Figure 9A:
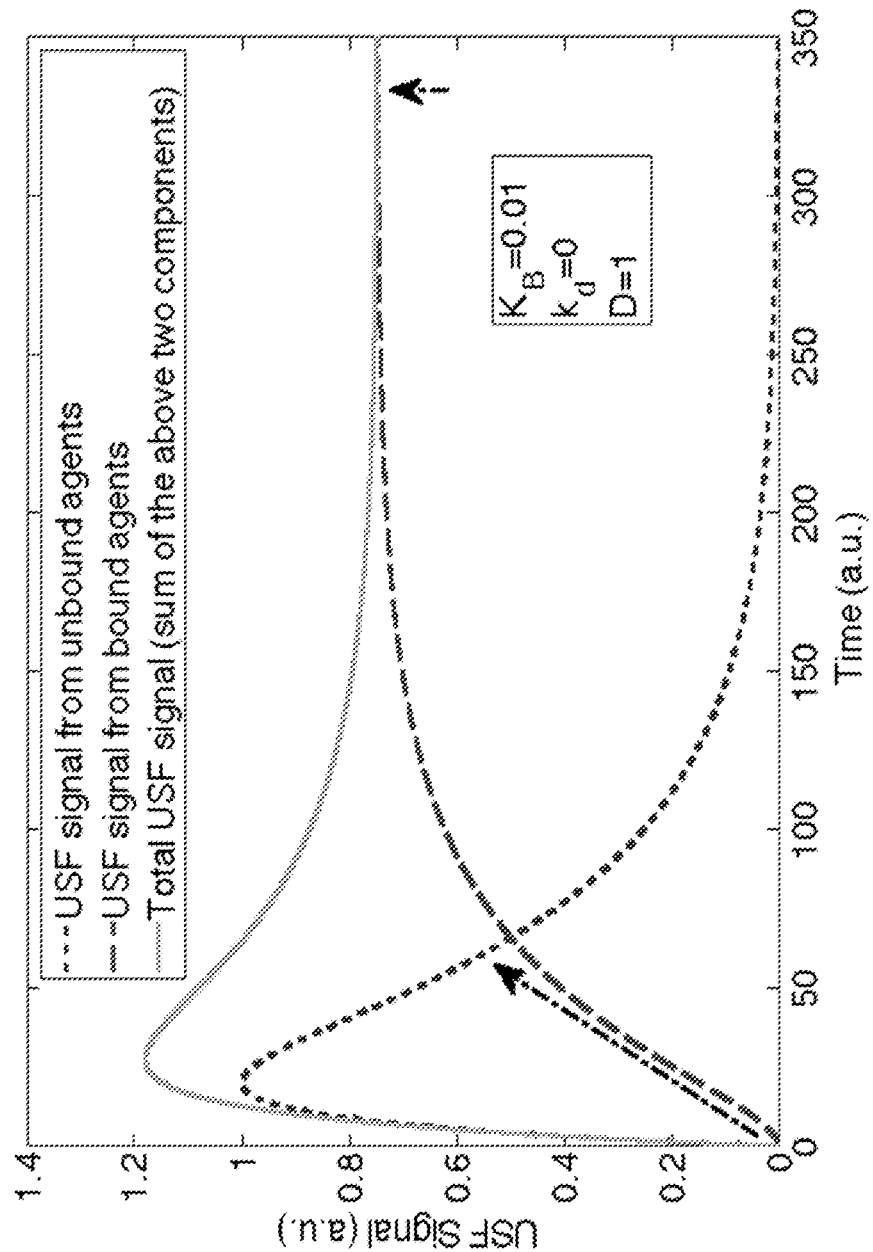
FIGS. 9A-9D illustrate plots of binding dynamics of targeting ultrasound-switchable fluorophores at different conditions of Kb and Kd simulated from the two-compartment model of FIG. 7.
Figure 9B:
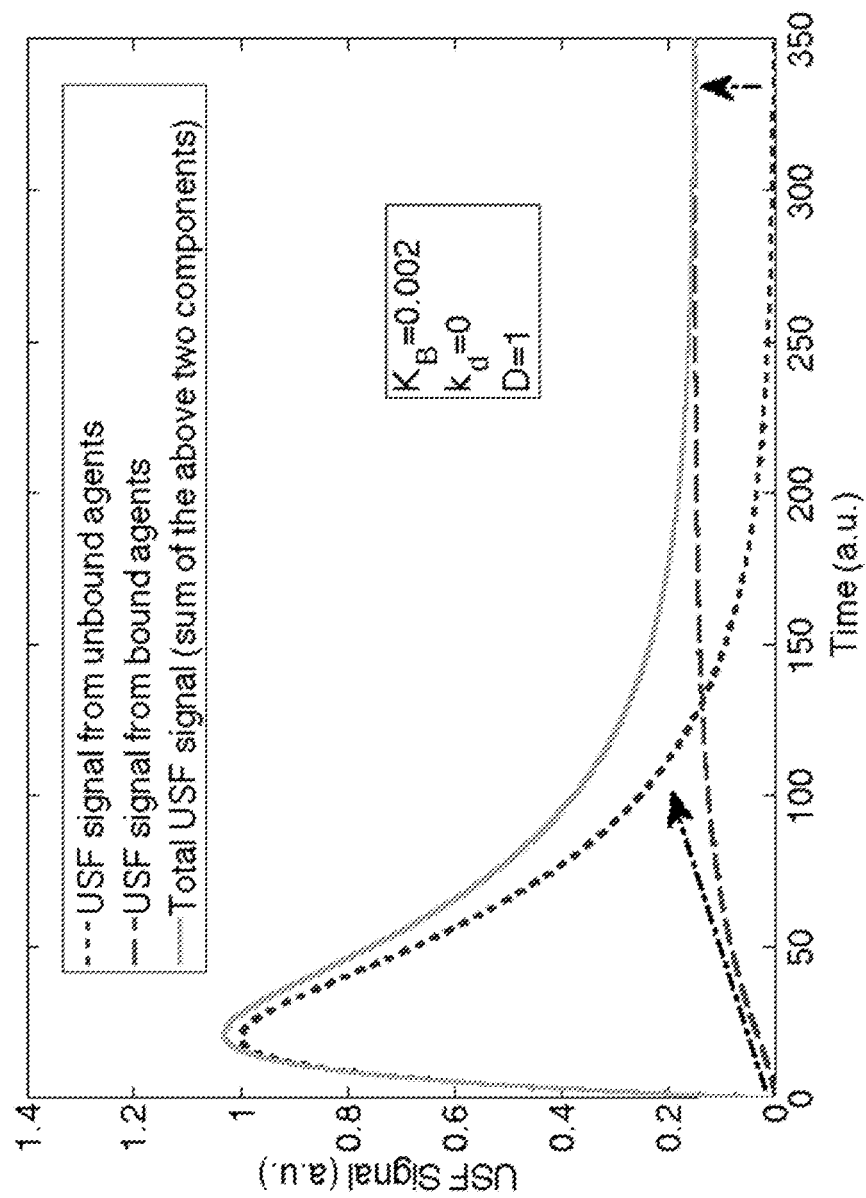
Figure 9C:
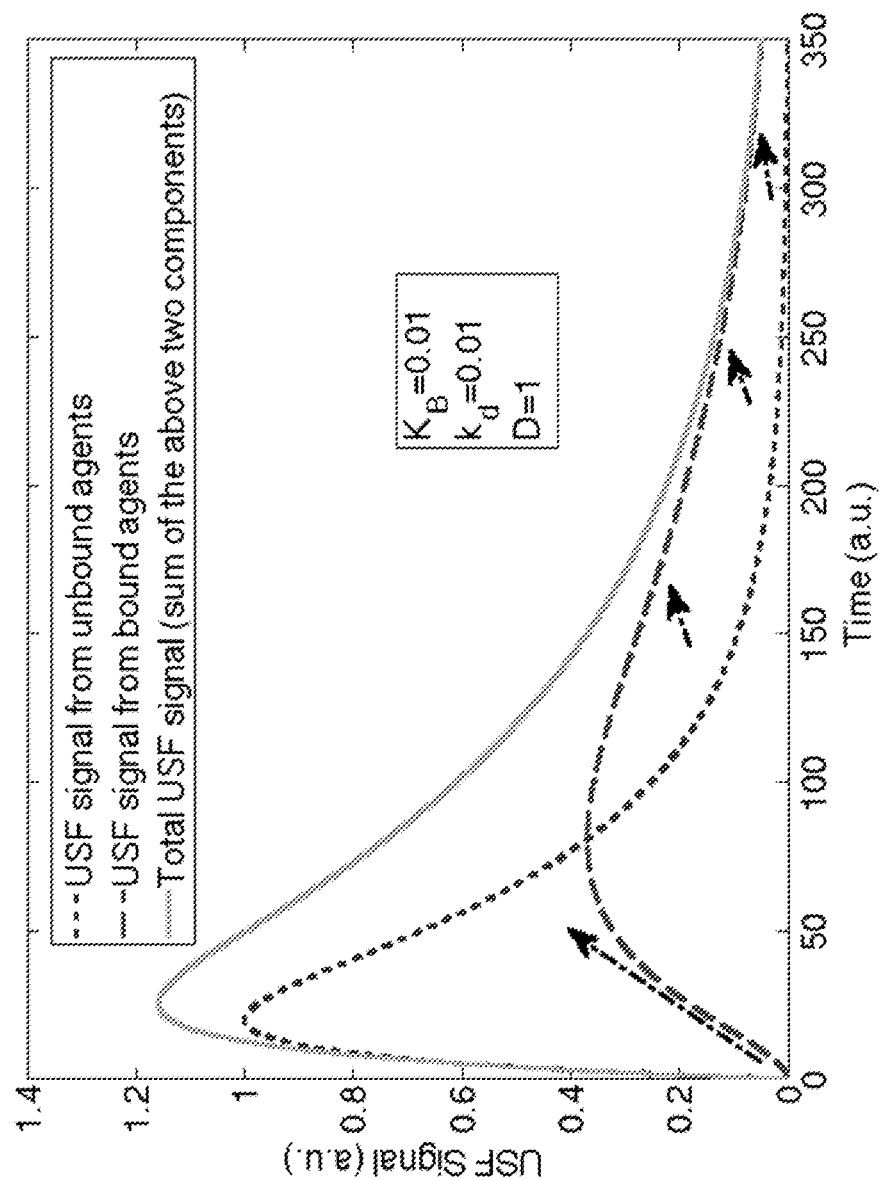
Figure 9D:
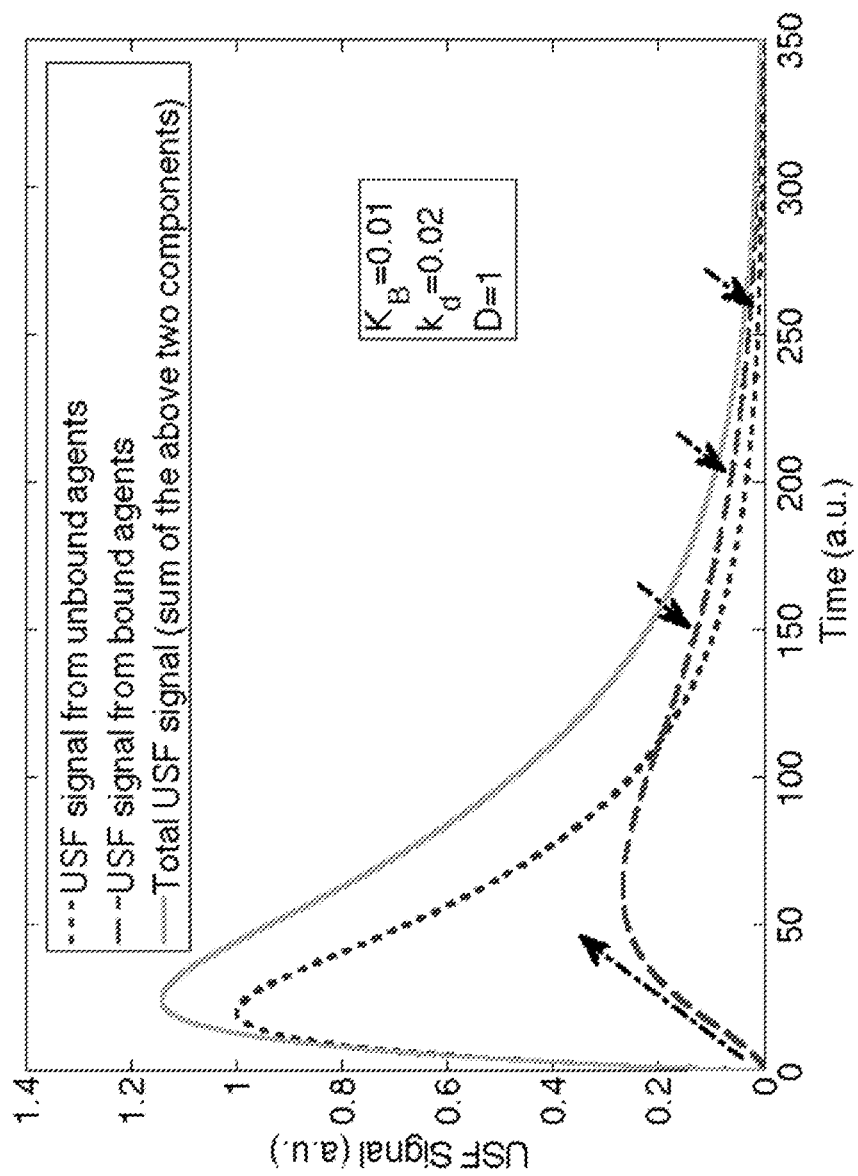

For example, FIGS. 9A-D show simulated signals from a bolus injection of contrast agents. The dotted and dashed lines respectively represent USF signals from bound and unbound agents (i.e. $A_E(t)$ and $A_V(t)$). The solid line shows the total USF signal (i.e. $A_T(t)$). FIG. 9A shows a case in which the binding rate constant is large ($K_B=0.01$) and the detaching rate constant is zero ($k_d=0$). When t>200 (a.u.), the total signal reaches a plateau and roughly equals to the signal from the bound agents. This scenario is necessary for conventional molecular imaging methods to be successful, i.e. the unbound agents are quickly washed out and the bound agents remain. FIG. 9B shows another case in which $K_B=0.002$ has been reduced 5-fold, and $k_d=0$, which is the same as FIG. 9(a). Although a final plateau can still be reached by the total signal (solid line), the plateau's value is reduced approximately-5-fold, degrading the sensitivity and SNR. FIGS. 9C and 9D show two more practical cases where $K_B$ remains 0.01 and $k_d=0.01$ or 0.02. After the peak, the total signal (solid line) never reaches a plateau. Thus, it is very difficult to judge when the best time is to image. Further, the signal from the bound contrast agent may never dominate or significantly dominate, which can lead to failure of conventional molecular imaging technologies due to the low specificity. In summary, conventional molecular imaging technologies can often only achieve high specificity in the special case shown in FIG. 9A. For other cases, conventional molecular imaging technologies often either fail or image with limited or poor specificity and sensitivity. However, the methods of USF multiplex imaging according to some embodiments described herein reconstructs the binding dynamics in all cases (reconstruct the dash lines) to achieve higher specificity and sensitivity.

EXAMPLE 4

Methods of Imaging In Vitro

Methods of in vitro USF imaging of the binding dynamics of the targeting ultrasound-switchable fluorophores and the non-targeting ultrasound-switchable fluorophores to cells in a flow chamber according to some embodiments described herein are carried out as follows.

Molecular conjugation of targeting and non-targeting moieties of USF ultrasound-switchable fluorophors (e.g. contrast agents) are through biotin-streptavidin conjugation, as described above and shown, for example, in FIG. 8. The targeting moieties are selected for VEGFR2 and $\alpha_v\beta_3$ biomarkers, as previously described.

Mouse angiosarcoma SVR cells and mouse skeletal myoblast (C2C12) cells is used, since SVR cells express both VEGFR2 and $\alpha_v\beta_3$ biomarkers, but C2C12 cells do not express either biomarkers.

Figure 10:
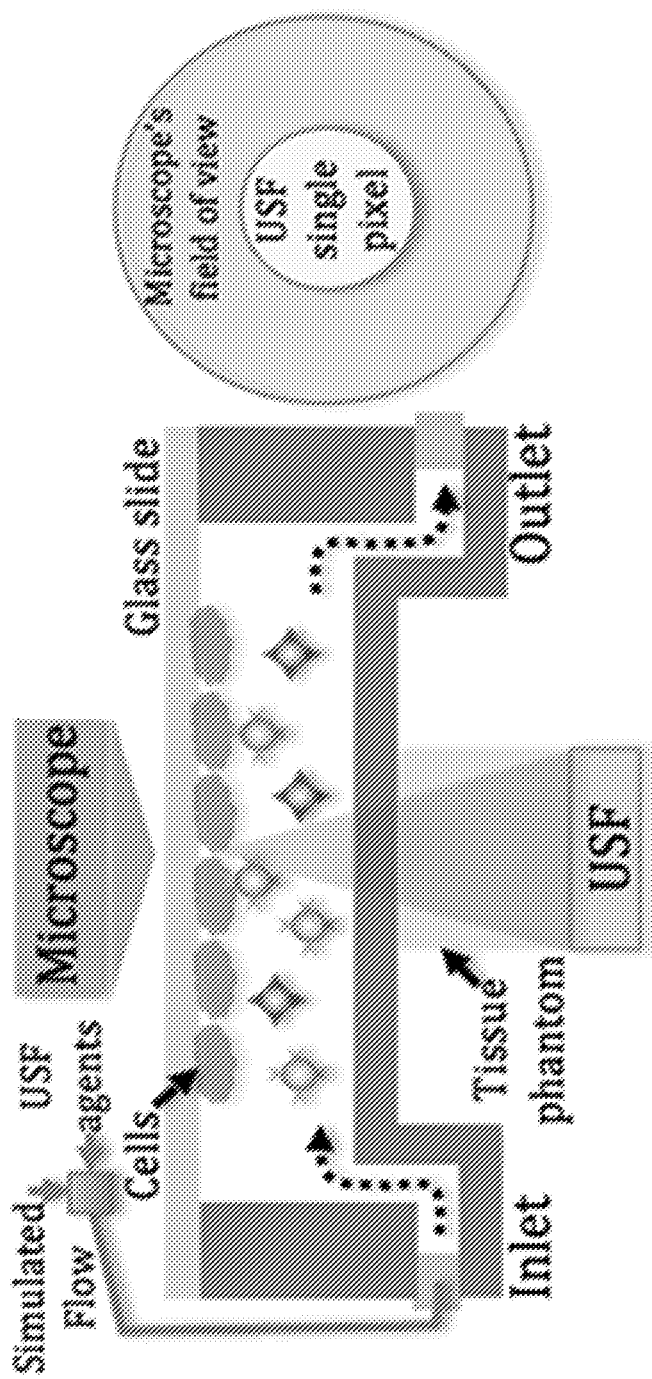
FIG. 10 illustrates an in vitro USF imaging system.

A parallel plate flow chamber (from Glycotech) is used to simulate blood flow with controlled shear stress (see FIG. 10). SVR and C2C12 cells are respectively cultured and fixed on two different microscope glass slides. A third glass slide without any fixed cells is used as a secondary negative control. As shown in FIG. 10 (left side), an upside down geometry of the flow chamber allows gas-filled particles to float to and interact with the cell surface during transit. A 2-to-1 connector is used to generate a constant flow and to inject a bolus of multi-color targeting and non-targeting contrast agents (i.e. targeting ultrasound switchable fluorophores and non-targeting ultrasound switchable fluorophores). The USF imaging system is positioned at the bottom of the cell sample and images the dynamic binding and detaching of the targeting agents to cells. A multi-color fluorescence microscope is positioned on the top of the sample and focused on the cell plane, and records the binding and detaching of the agents. The ultrasound focus will be translated inside the microscope's field of view (FIG. 10, right side) and its location and size are determined via a needle hydrophone. Thus, only those agents in the ultrasound focus will be counted via the microscope. Immunocytochemical (ICC) analysis is conducted to validate the existence of the biomarkers in the imaging area. Results from the two imaging methods are compared for different samples (such as positive, negative cells and no cells) and different experimental conditions (such as VEGFR2, $\alpha_v\beta_3$ and both, and different flow stress). Similarity from the two systems and the significant difference between different samples are statistically analyzed via commercial software (Stata®).

The invention claimed is:
1. A method of imaging comprising:
    (a) disposing a population of first targeting ultrasound-switchable fluorophores and a population of second non-targeting ultrasound-switchable fluorophores in an environment;
    (b) exposing the environment to an ultrasound beam to create an activation region within the environment;
    (c) disposing the populations of first targeting fluorophores and the second non-targeting fluorophores within the activation region to switch the first targeting fluorophores and the second non-targeting fluorophores from an off state to an on state;
    (d) exposing the activation region with one or more beams of electromagnetic radiation, thereby exciting the population of first targeting fluorophores and second non-targeting fluorophores;
    (e) detecting a first photoluminescence signal emitted by the population of first targeting fluorophores, and a second photoluminescence signal emitted by the population of second non-targeting fluorophores;
    (f) determining a photoluminescence property of the population of second non-targeting fluorophores from the second photoluminescence signal; and
    (g) using the determined photoluminescence property of the population of second non-targeting fluorophores to deconvolute the first photoluminescence signal into the population of first targeting fluorophores bound and unbound to a first target binding element in the environment.
2. The method of claim 1, wherein the first targeting fluorophores reversibly binds to the first target binding element.
3. The method of claim 1, wherein the first targeting fluorophores comprises a first targeting moiety.
4. The method of claim 3, wherein the first targeting moiety is a first antibody.
5. The method of claim 4, wherein the first antibody is anti-VEGFR2.
6. The method of claim 4, wherein the first antibody is anti-$\alpha_v\beta_3$.

7. The method of claim 3, wherein the second non-targeting fluorophores comprises a non-targeting moiety.
8. The method of claim 7, wherein the non-targeting moiety is a negative control of the first targeting moiety.
9. The method of claim 7, wherein the non-targeting moiety is an isotype-matched control antibody.
10. The method of claim 7, wherein a physicochemical behavior of unbound first targeting fluorophores in the environment is similar to a physicochemical behavior of unbound second non-targeting fluorophores in the environment.
11. The method of claim 1, wherein the environment is biological tissue, biological phantom material, or tissue-mimicking phantom material.
12. The method of claim 1, wherein the first targeting fluorophore has a first excitation wavelength maximum.
13. The method of claim 12, wherein the second non-targeting fluorophores has a second excitation wavelength maximum that is different from the first excitation wavelength maximum to avoid or reduce spectral cross-talk.
14. The method of claim 1, wherein the first targeting fluorophores has a first excitation wavelength maximum, and the second non-targeting fluorophores has a second excitation wavelength maximum.
15. The method of claim 14, wherein the first excitation wavelength maximum is equal to the second excitation wavelength maximum.
16. The method of claim 15, wherein the beam of electromagnetic radiation has a wavelength maximum equal to the first excitation wavelength maximum and equal to the second excitation wavelength maximum.
17. The method of claim 14, wherein the first excitation wavelength maximum is different from the second excitation wavelength maximum.
18. The method of claim 17, wherein the activation region is exposed to a first beam of electromagnetic radiation with the first excitation wavelength maximum, and a second beam of electromagnetic radiation with the second excitation wavelength maximum.
19. The method of claim 18, wherein the first beam of electromagnetic radiation and the second beam of electromagnetic radiation are exposed to the environment sequentially.
20. The method of claim 18, wherein the first beam of electromagnetic radiation and the second beam of electromagnetic radiation are exposed to the environment simultaneously.
21. The method of claim 1, wherein an emission profile of a wavelength maximum of the emitted first photoluminescence signal is different from an emission profile of a wavelength maximum of the emitted second photoluminescence signal.
22. The method of claim 21, wherein the emission profiles of the emitted first photoluminescence and the emitted second photoluminescence are individually selected from one of 680-710 nm, 740-770 nm, or >840 nm.
23. The method of claim 1, wherein:
    the first photoluminescence signal is detected with a first detector or first detector channel; and
    the second photoluminescence signal is detected with a second detector or second detector channel.
24. The method of claim 23, wherein:
    the second detector is off when the first photoluminescence signal is detected; and
    the first detector is off when the second photoluminescence signal is detected.

25. The method of claim 23, wherein the first detector detects the first photoluminescence signal simultaneously as the second detector detects the second photoluminescence signal.

26. The method of claim 1 further comprising:
   ($a_2$) disposing a population of third targeting ultrasound-switchable fluorophores in the environment;
   ($c_2$) disposing the population of third targeting fluorophores within the activation region to switch the population of third targeting fluorophores from an off state to an on state; and
   ($d_2$) exposing the activation region to the one or more beams of electromagnetic radiation, thereby exciting the population of third targeting fluorophores.

27. The method of claim 26, further comprising:
   ($e_2$) detecting a third photoluminescence signal emitted by the population of third targeting fluorophores;
   ($f_2$) determining a photoluminescence property of the population of second non-targeting fluorophores from the second photoluminescence signal; and
   ($g_2$) using the determined photoluminescence property of the population of second non-targeting fluorophores to deconvolute the third photoluminescence signal into the population of third targeting fluorophores bound and unbound to a third target binding element in the environment.

28. The method of claim 27, wherein the third targeting fluorophore reversibly binds to a third binding element in the environment.

29. The method of claim 28, wherein the third binding element is different from the first binding element.

* * * * *